(12) United States Patent
Amer

(10) Patent No.: US 7,819,121 B2
(45) Date of Patent: Oct. 26, 2010

(54) EXTERNAL PENILE PROSTHESIS, COMBINATION OF PROSTHESIS AND LOOSE-FITTING CONDOM, AND METHOD OF USING CONDOM

(75) Inventor: Ame M. Amer, 18995 Leslie Street, Sharon, Ontario (CA) L0G 1V0

(73) Assignee: Ame M. Amer, Newmarket (CA)

( * ) Notice: Subject to any disclaimer, the term of this patent is extended or adjusted under 35 U.S.C. 154(b) by 1407 days.

(21) Appl. No.: 11/252,809

(22) Filed: Oct. 19, 2005

(65) Prior Publication Data
US 2006/0030750 A1   Feb. 9, 2006

Related U.S. Application Data

(63) Continuation-in-part of application No. PCT/CA2004/000525, filed on Apr. 7, 2004.

(30) Foreign Application Priority Data

Apr. 23, 2003   (CA) .................................. 2426350

(51) Int. Cl.
*A61F 6/02* (2006.01)
*A61F 6/04* (2006.01)
*A61F 5/44* (2006.01)
*A61B 5/00* (2006.01)
*A61M 1/00* (2006.01)

(52) U.S. Cl. ........................ 128/842; 128/844; 128/917; 128/918; 604/327; 604/347; 604/351; 600/38; 600/39; 600/41

(58) Field of Classification Search ................. 128/842, 128/844, 918, 830, 834, 835, 837; 604/347–353; 600/38–41
See application file for complete search history.

(56) References Cited

U.S. PATENT DOCUMENTS

| 4,332,243 | A | * | 6/1982 | Gutnick ...................... 128/844 |
| 4,640,270 | A | | 2/1987 | Chin |
| 4,738,357 | A | | 4/1988 | Martin et al. |
| 4,846,197 | A | | 7/1989 | Benjamin |

(Continued)

FOREIGN PATENT DOCUMENTS

CA         2069326         4/1991

(Continued)

*Primary Examiner*—Patricia M Bianco
*Assistant Examiner*—Brandon Jackson
(74) *Attorney, Agent, or Firm*—Rothwell, Figg, Ernst & Manbeck, P.C.

(57) ABSTRACT

To use a loose-fitting condom, a penis or prosthesis is covered loosely with a condom having a loose-fitting portion. The loose-fitting portion is twisted so that the loose-fitting portion closely covers the penis or prosthesis. The loose-fitting portion is then secured in the twisted state. An external penile prosthesis is provided, which includes a generally tubular body portion and a head portion. The head portion can be rotatable about the central axis of the body portion or include a plurality of flaps swingably attached to the body portion for adjusting an opening between the flaps. Further provided is a combination of the prosthesis and a loose-fitting condom. The condom has a flexible sheath which has a loose-fitting portion sized for loosely covering a penis or the prosthesis. The combination may further include a holder for holding the loose-fitting condom in a twisted position.

104 Claims, 38 Drawing Sheets

U.S. PATENT DOCUMENTS

| | | | | |
|---|---|---|---|---|
| 4,875,491 A | | 10/1989 | Parrone | |
| 5,036,863 A | | 8/1991 | Wheeler | |
| 5,113,873 A | | 5/1992 | Boarman | |
| 5,163,449 A | | 11/1992 | Van der Valk | |
| 5,269,320 A | | 12/1993 | Hunnicutt | |
| 5,327,911 A | | 7/1994 | Pien | |
| 5,351,698 A | | 10/1994 | Wheeler et al. | |
| 5,437,286 A | | 8/1995 | Stratton | |
| 5,454,379 A | | 10/1995 | Shepherd | |
| 5,515,862 A | | 5/1996 | Artsi et al. | |
| 5,638,829 A | | 6/1997 | Najor | |
| 5,823,939 A | * | 10/1998 | Tsagarakis | 600/38 |
| 5,836,308 A | * | 11/1998 | Alla et al. | 128/844 |
| 5,842,970 A | | 12/1998 | Lakusiewicz | |
| 5,868,137 A | | 2/1999 | Brown | |
| 6,478,027 B1 | | 11/2002 | Serrano et al. | |
| 6,776,755 B1 | * | 8/2004 | Raskin | 600/39 |
| 2002/0022760 A1 | | 2/2002 | Orten | |

FOREIGN PATENT DOCUMENTS

| | | | |
|---|---|---|---|
| CA | 2084903 | | 6/1994 |
| CA | 1334270 | | 2/1995 |
| CA | 2017068 | | 7/1998 |
| DE | 20203927 | * | 3/2002 |

* cited by examiner

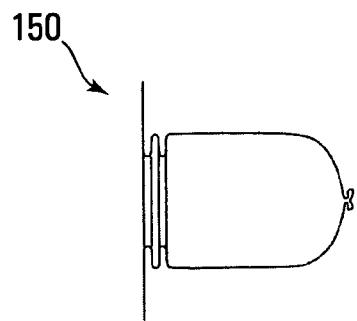
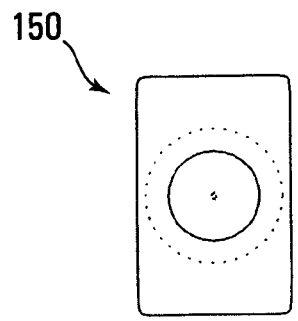
FIG. 5A          FIG. 5B
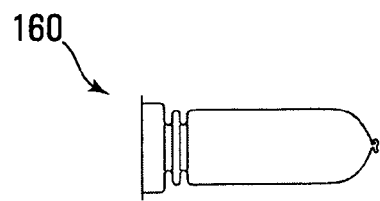
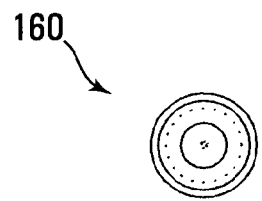
FIG. 6A          FIG. 6B
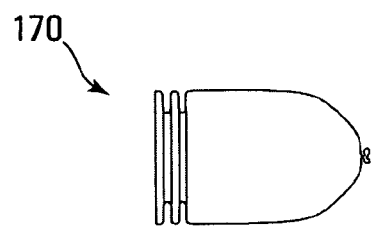
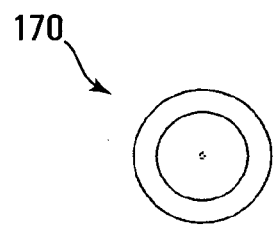
FIG. 7A          FIG. 7B
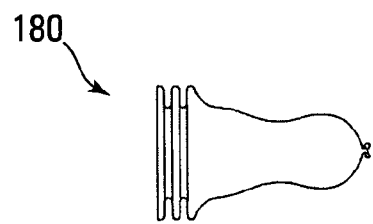
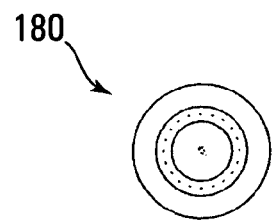
FIG. 8A          FIG. 8B

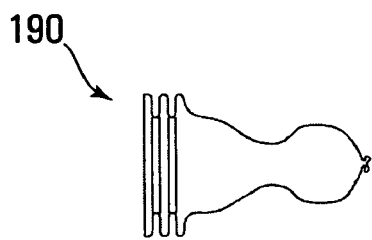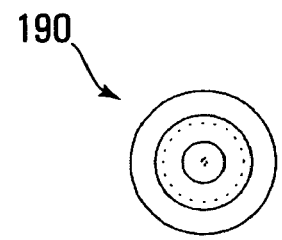
FIG. 9A  FIG. 9B
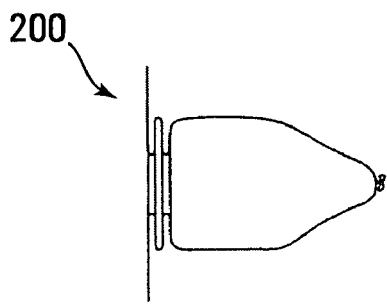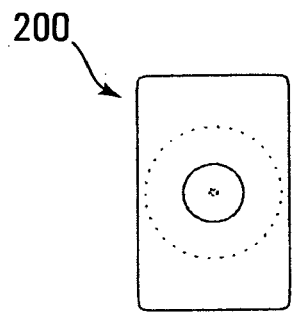
FIG. 10A  FIG. 10B
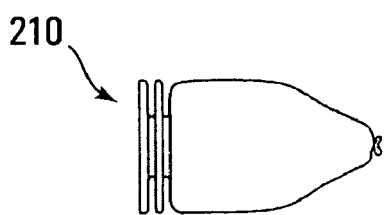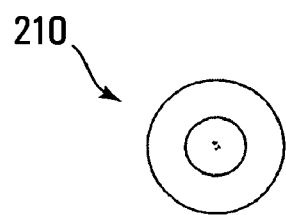
FIG. 11A  FIG. 11B
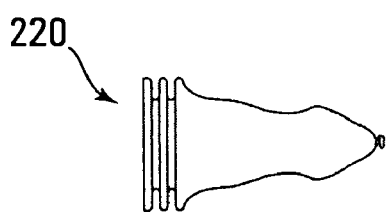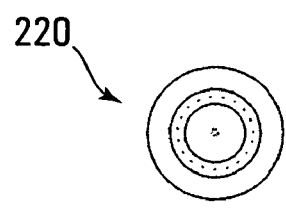
FIG. 12A  FIG. 12B

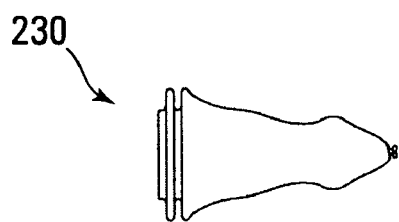
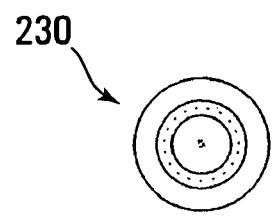
FIG. 13A  FIG. 13B
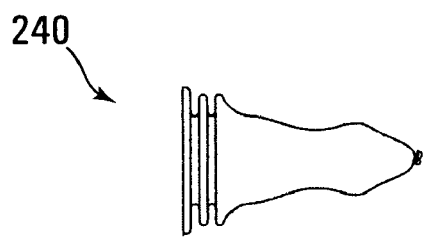
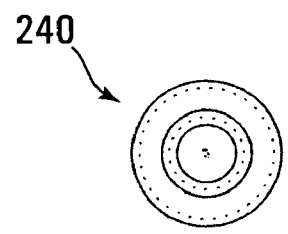
FIG. 14A  FIG. 14B
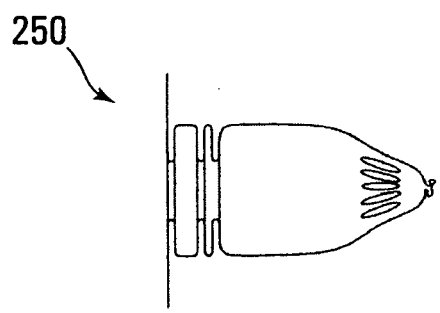
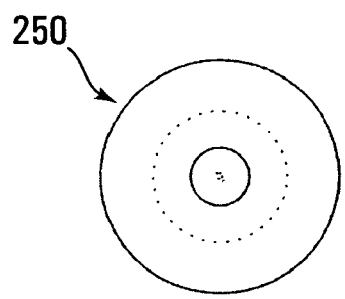
FIG. 15A  FIG. 15B
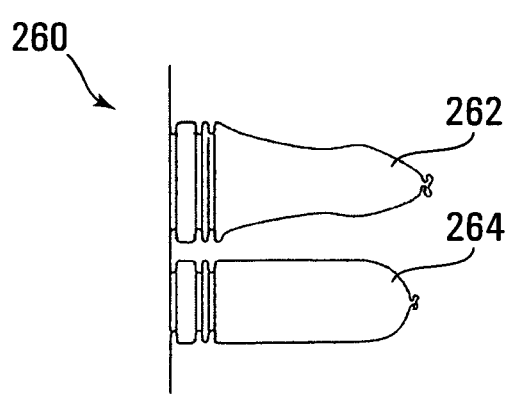
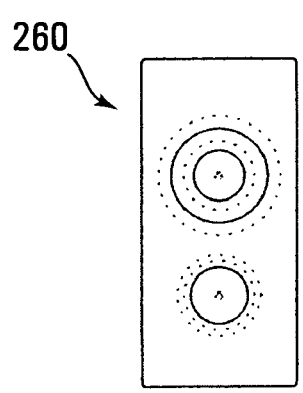
FIG. 16A  FIG. 16B

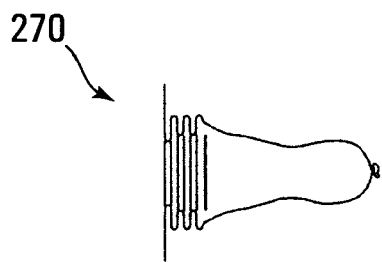
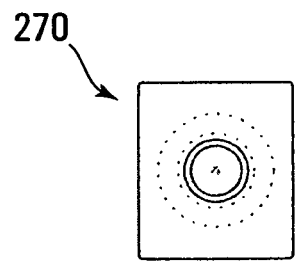
FIG. 17A      FIG. 17B
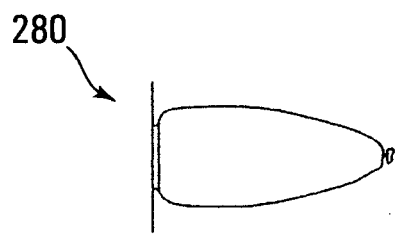
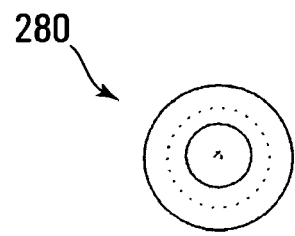
FIG. 18A      FIG. 18B
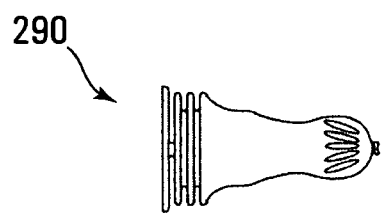
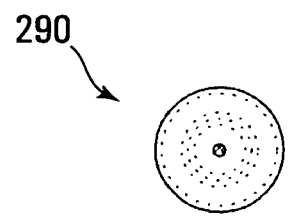
FIG. 19A      FIG. 19B
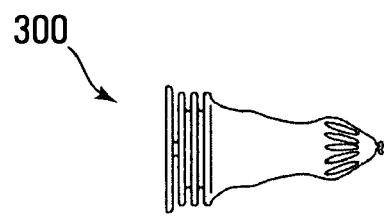
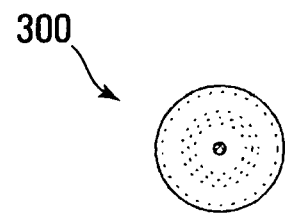
FIG. 20A      FIG. 20B

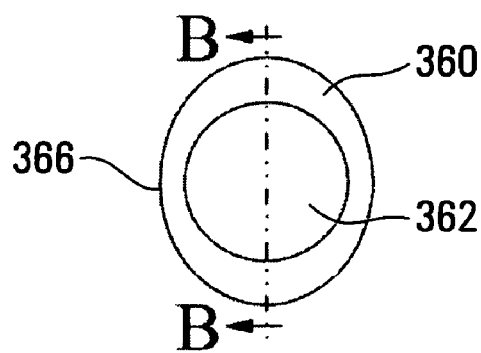
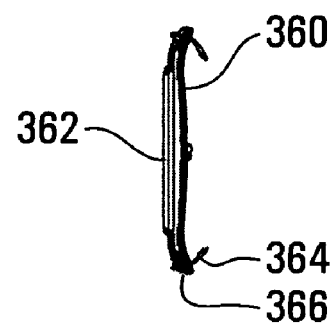
FIG. 26A                FIG. 26B
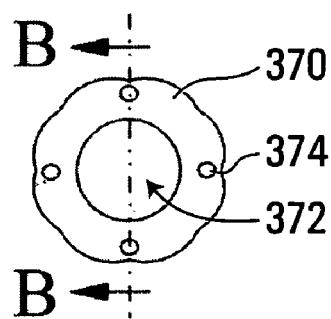
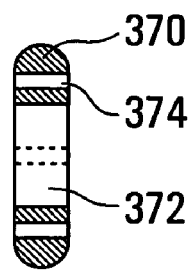
FIG. 27A                FIG. 27B

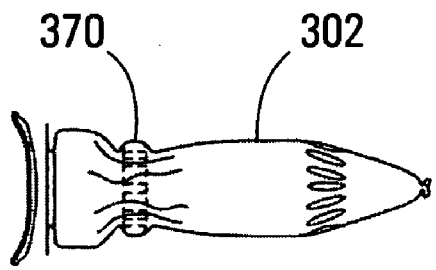
FIG. 31
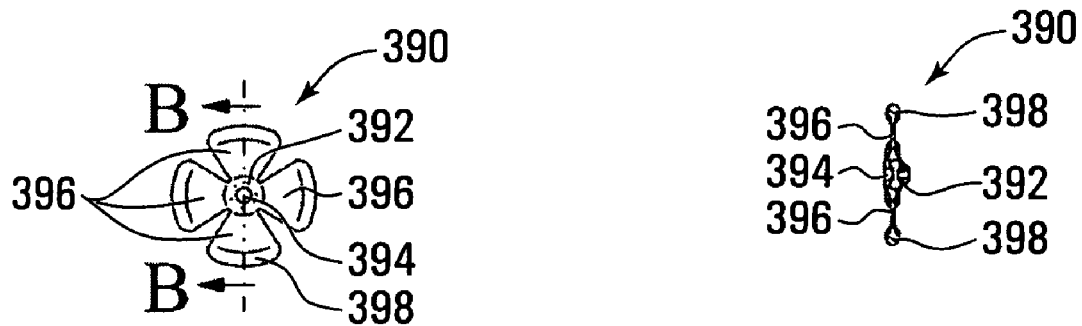
FIG. 32A  FIG. 32B
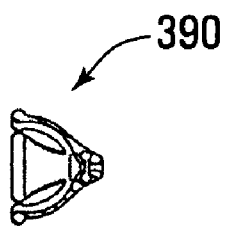
FIG. 32C

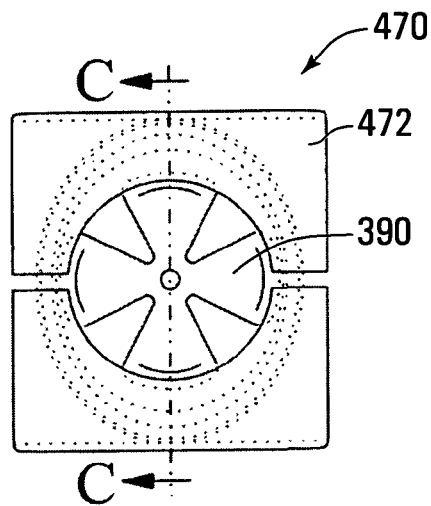 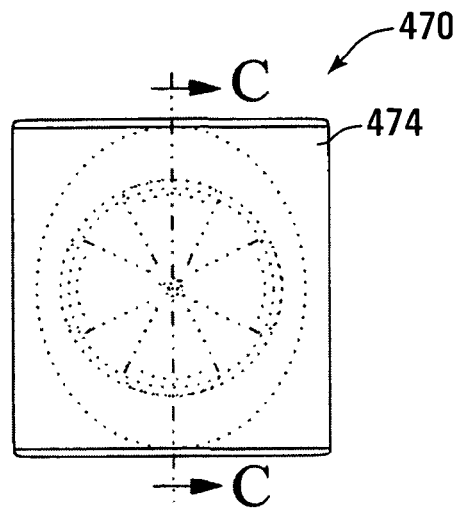
FIG. 40A  FIG. 40B
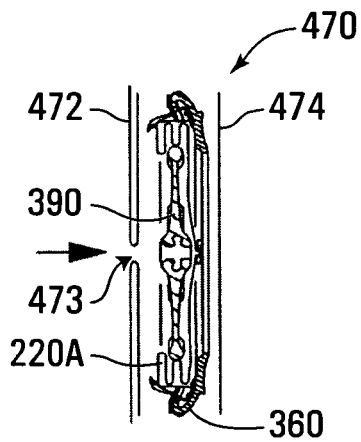 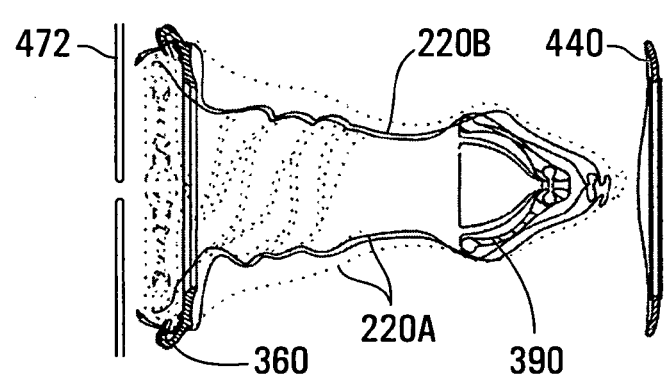
FIG. 40C  FIG. 40D
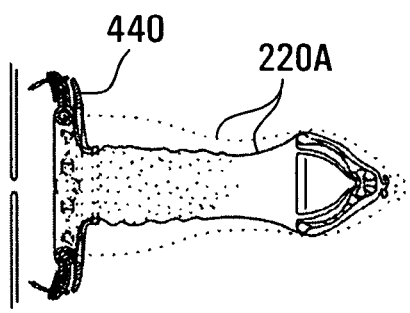
FIG. 40E

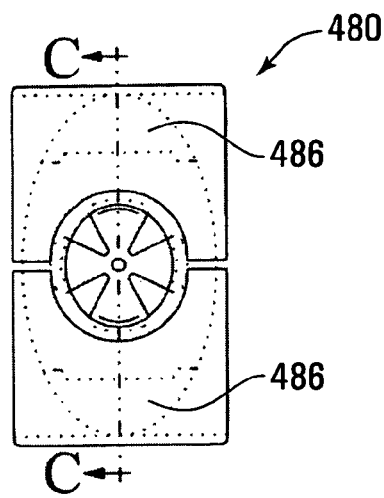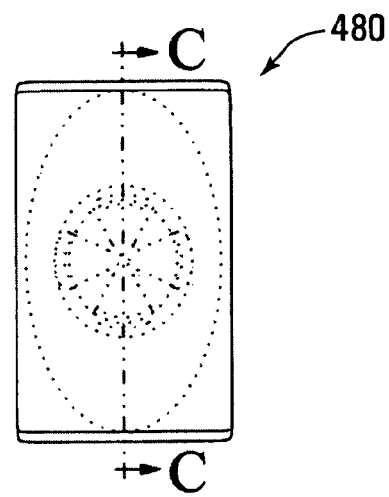
FIG. 41A  FIG. 41B
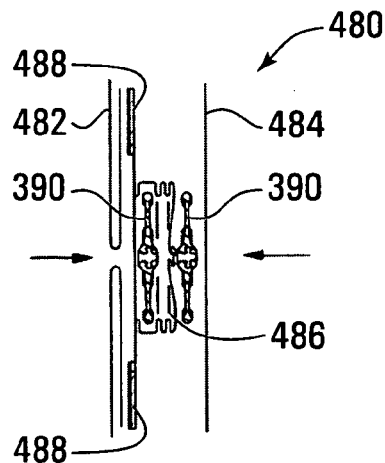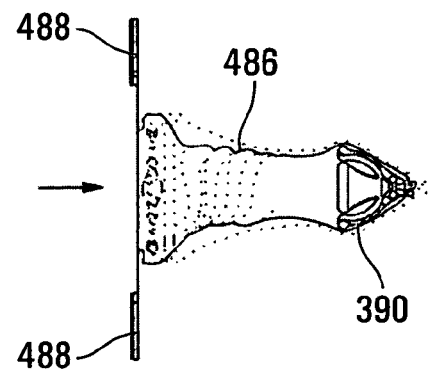
FIG. 41C  FIG. 41D
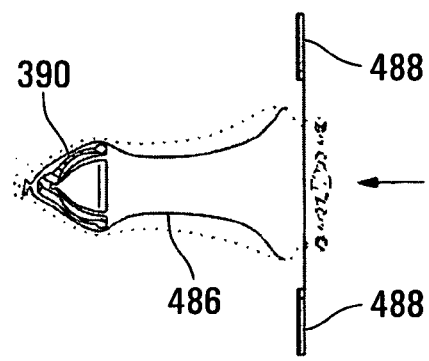
FIG. 41E

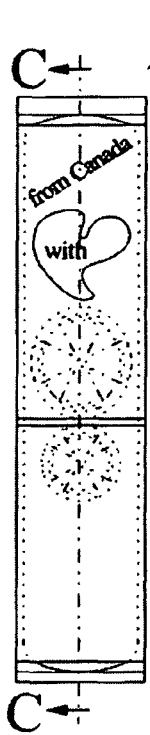
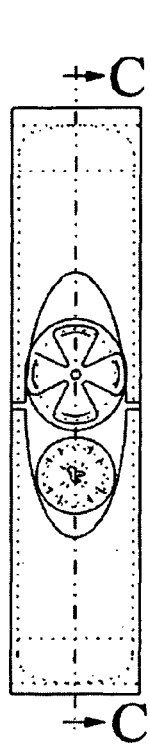
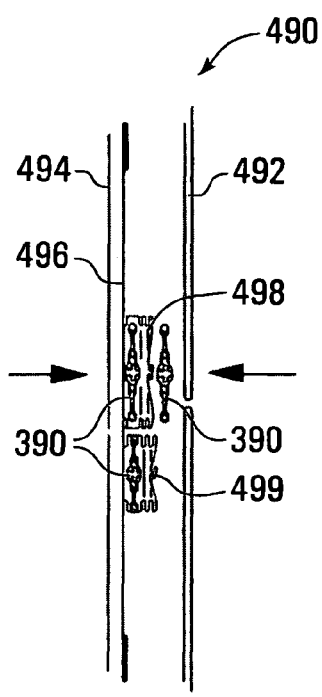
FIG. 42A  FIG. 42B  FIG. 42C
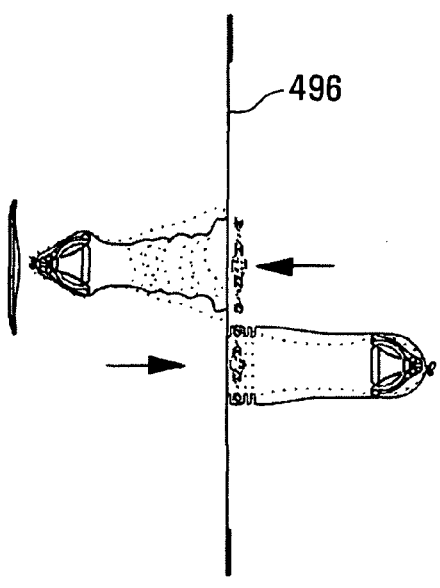
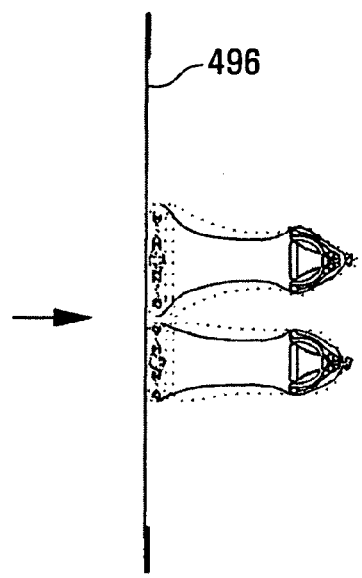
FIG. 42D  FIG. 42E

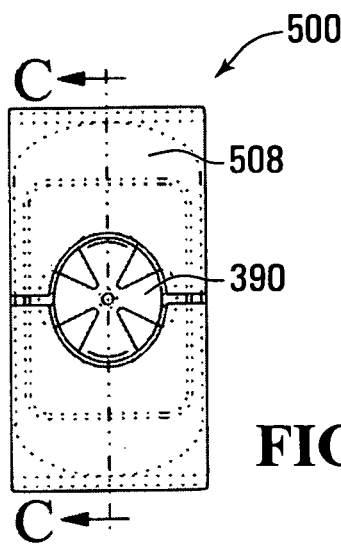
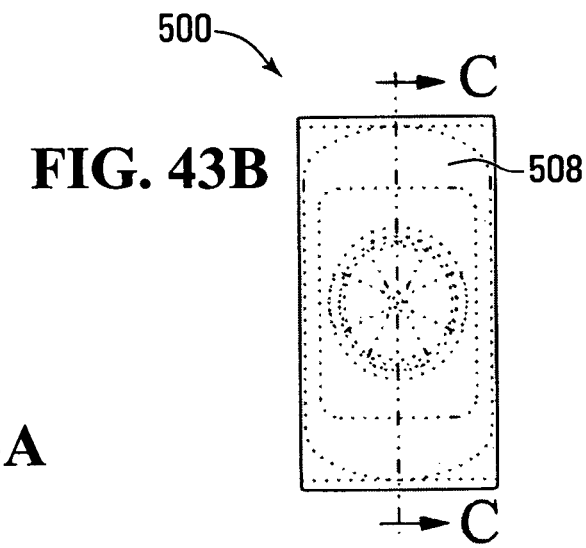
FIG. 43A
FIG. 43B
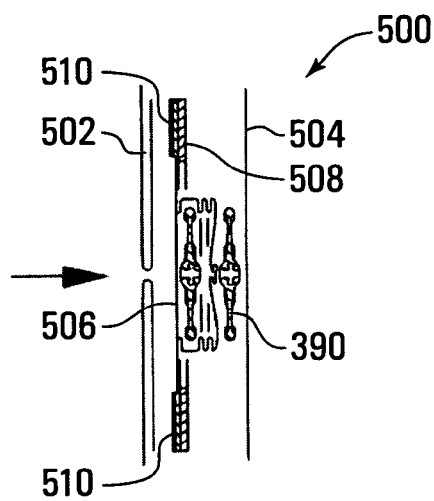
FIG. 43C
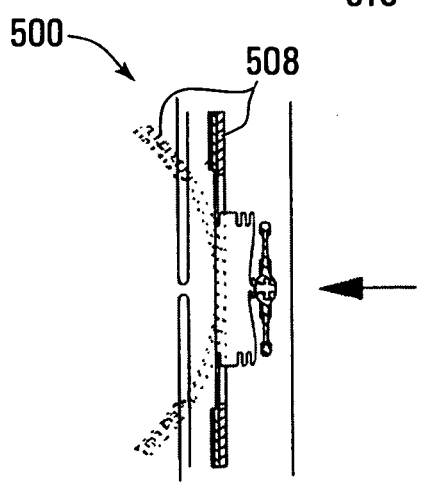
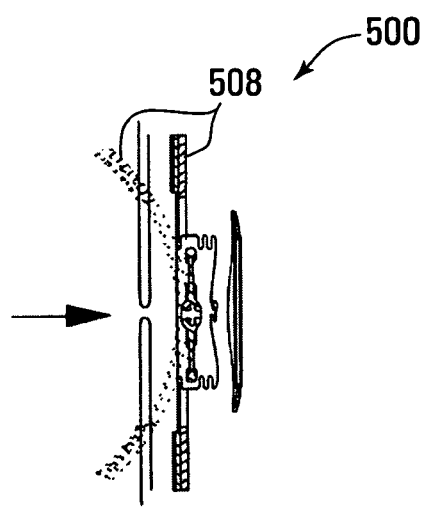
FIG. 43D
FIG. 43E

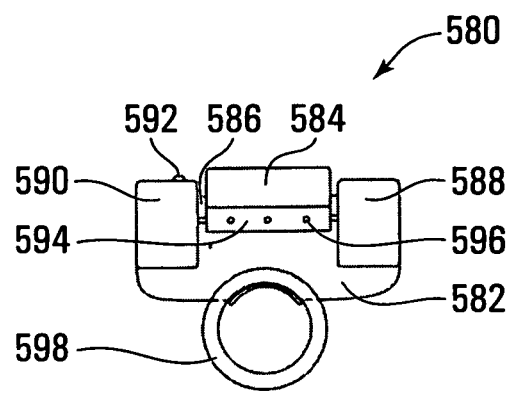 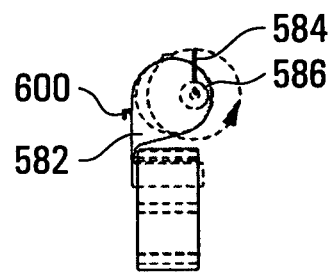
FIG. 55A        FIG. 55B
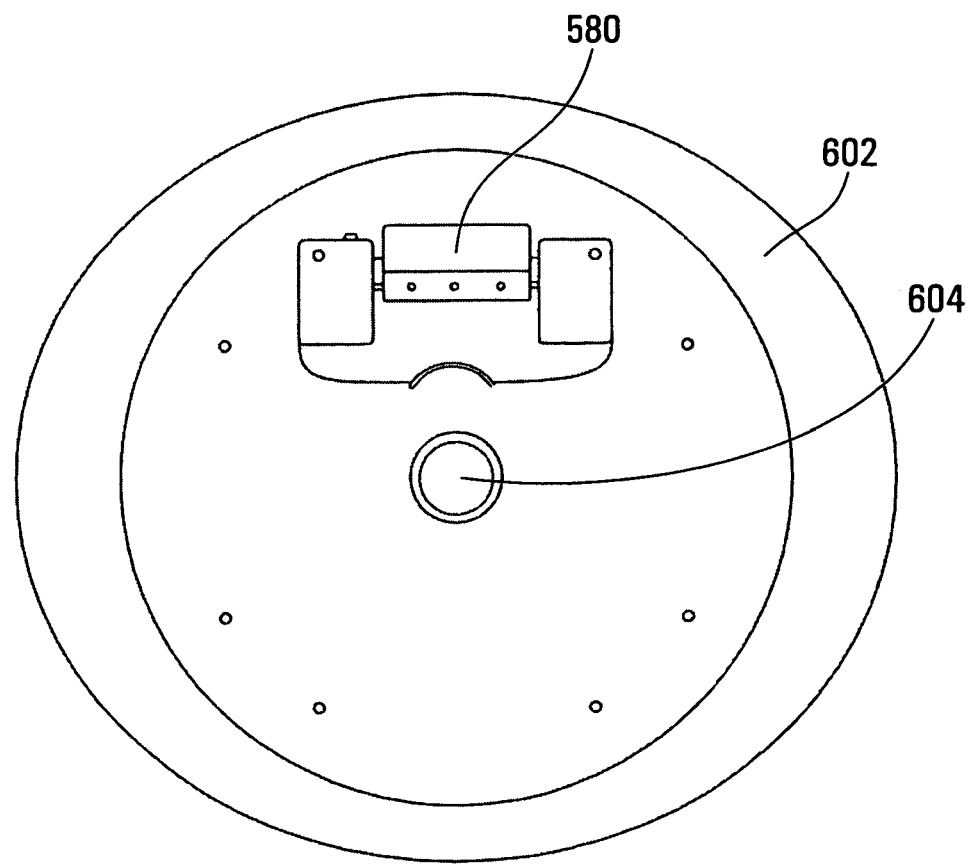
FIG. 56A

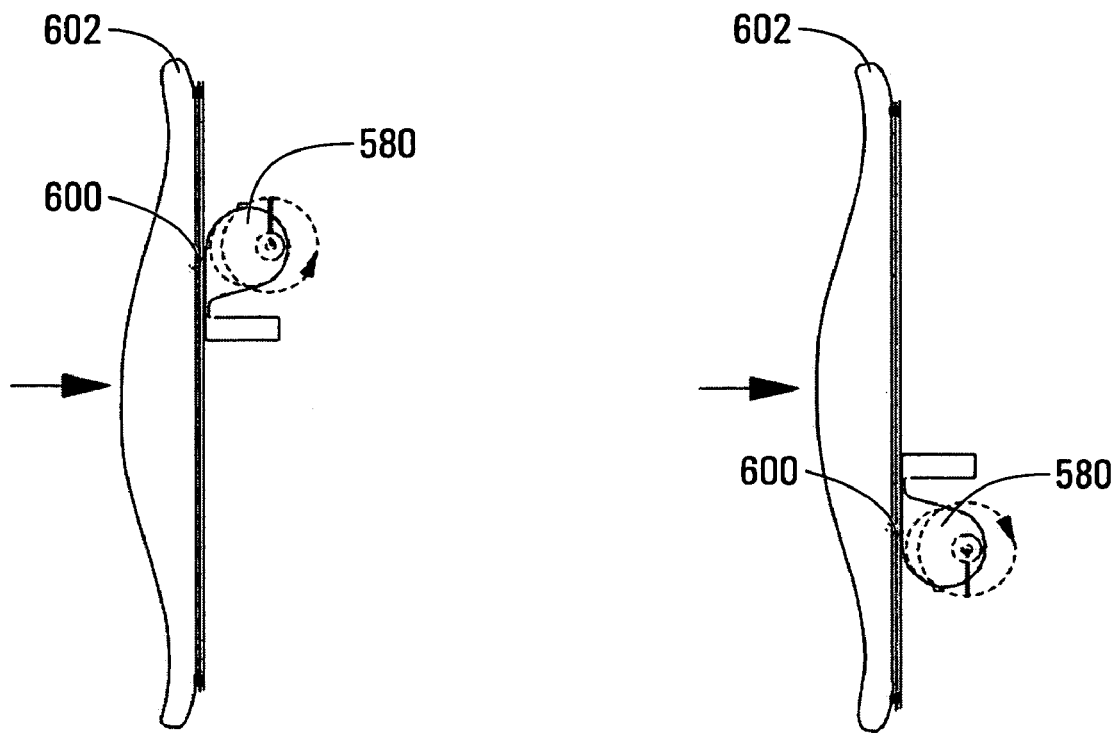
FIG. 56B  FIG. 56C
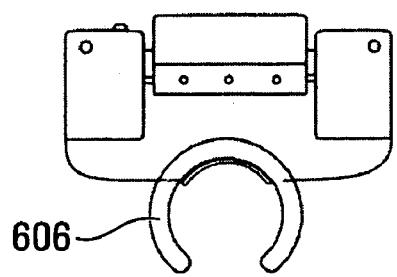
FIG. 57

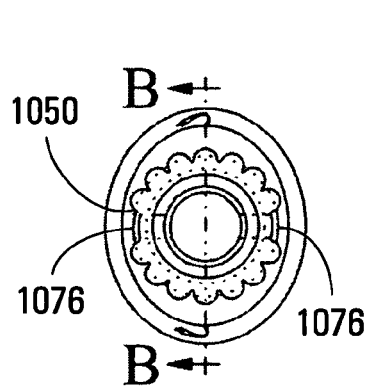
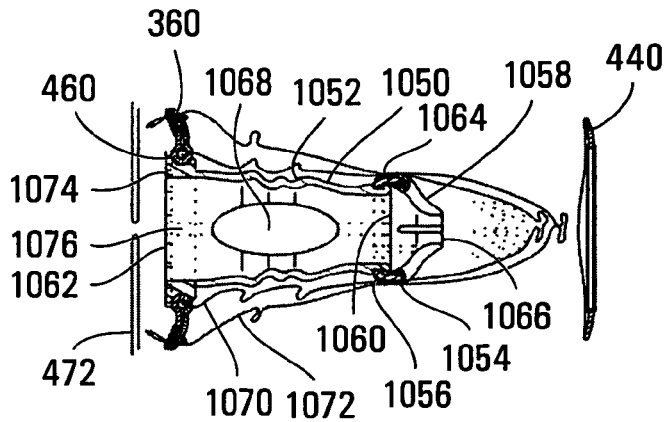
FIG. 64A  FIG. 64B
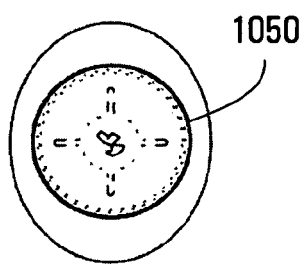
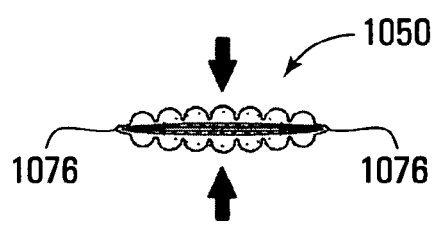
FIG. 64C  FIG. 65
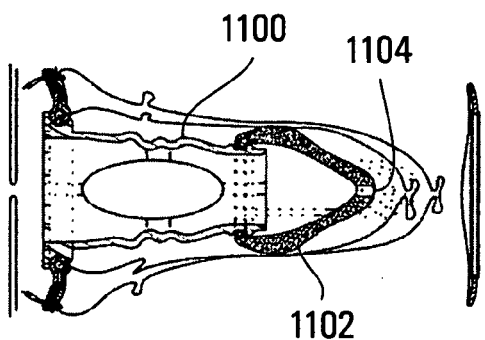
FIG. 66

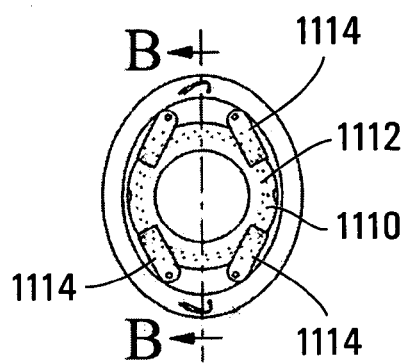
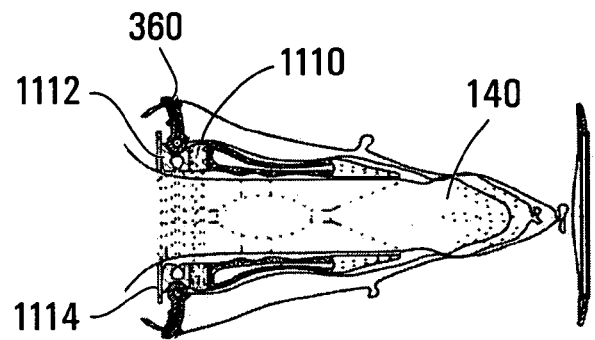
FIG. 67A          FIG. 67B
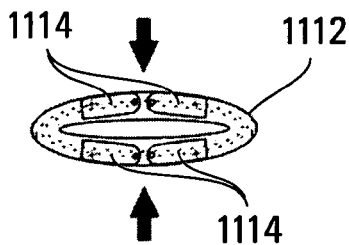
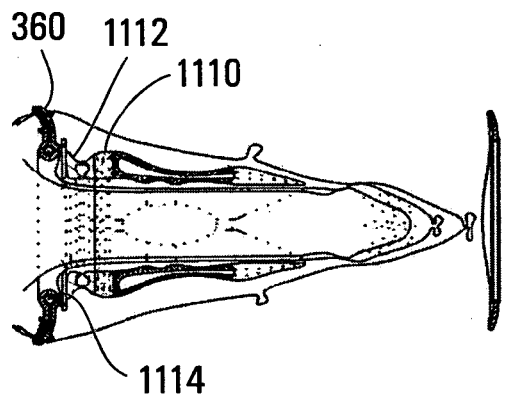
FIG. 67C          FIG. 67D
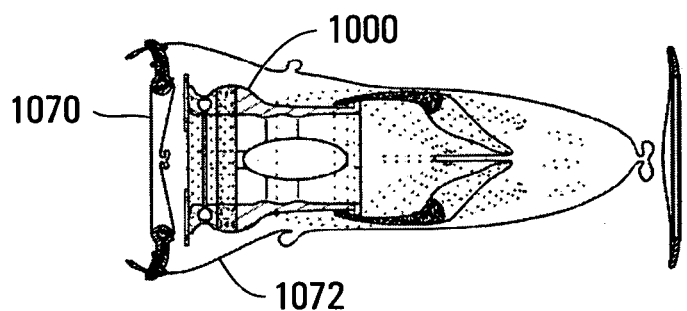
FIG. 68

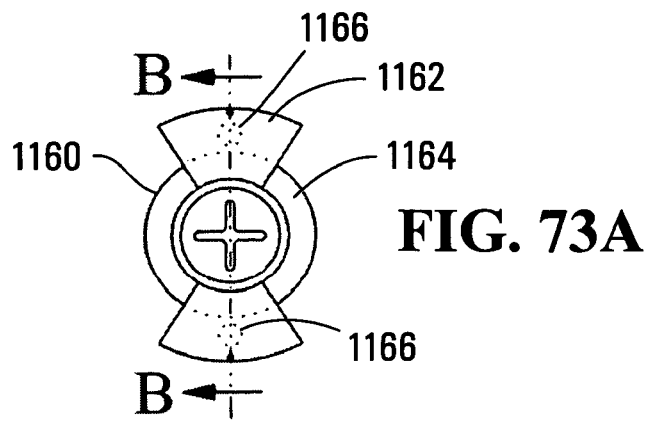
FIG. 73A
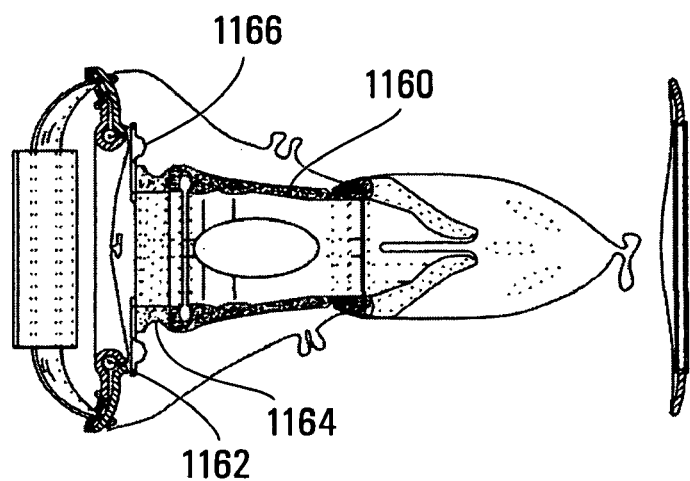
FIG. 73B
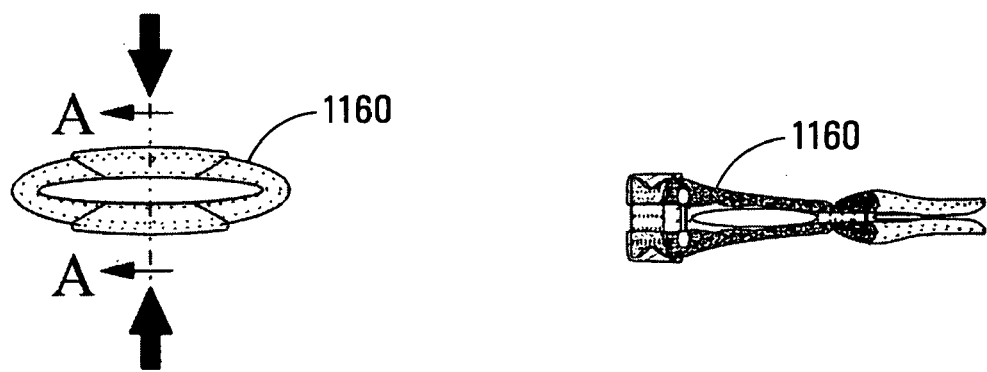
FIG. 73C
FIG. 73D

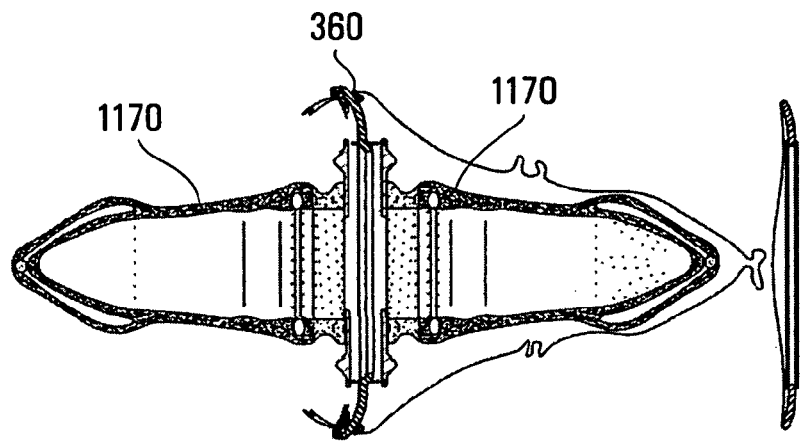
FIG. 74
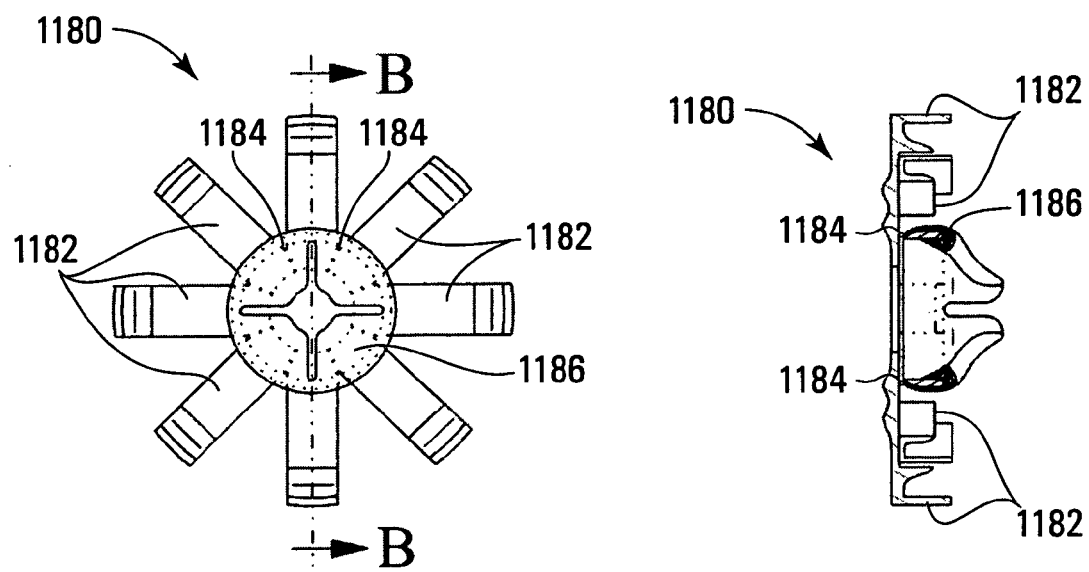
FIG. 75A  FIG. 75B

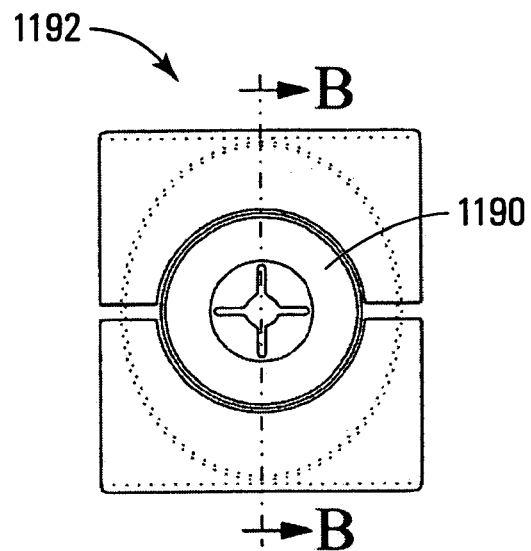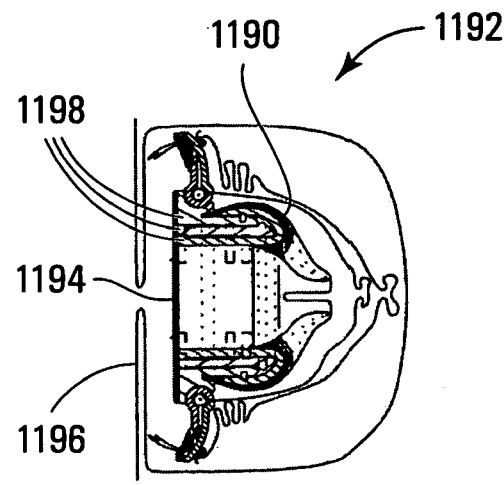
FIG. 76A     FIG. 76B
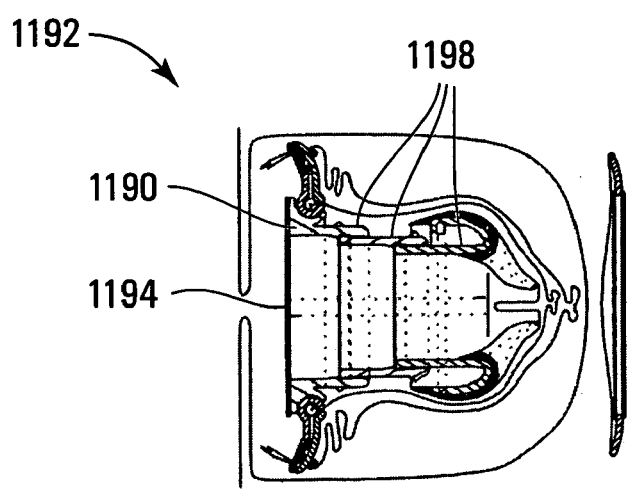
FIG. 76C

EXTERNAL PENILE PROSTHESIS, COMBINATION OF PROSTHESIS AND LOOSE-FITTING CONDOM, AND METHOD OF USING CONDOM

CROSS-REFERENCE TO RELATED APPLICATION

This is a continuation-in-part of PCT International Application PCT/CA2004/000525, with an international filing date of Apr. 7, 2004, and claiming the benefits of Canadian Patent Application No. 2,426,350, filed Apr. 23, 2003, the contents of each of which are incorporated herein by reference.

FIELD OF THE INVENTION

This invention relates generally to prophylactic devices and method of use, and more particularly to external penile prosthesis, combination of external penile prosthesis and loose-fitting condom, and method of using condom.

BACKGROUND OF THE INVENTION

Prophylactic devices such as condoms are widely used. They are useful for preventing pregnancy and sexually transmitted diseases (STD).

However, currently many users do not enjoy using condoms. For this reason, many people do not use condoms as often as they should, or not at all. Some problems with the conventional condoms and techniques for using them are that they may be uncomfortable to wear and inconvenient to use. For example, it can be difficult to put on a tight-fitting condom in a short time. Some users also find tight-fitting condoms are uncomfortable to wear. While loose-fitting condoms are known, they are not as popular as tight-fitting condoms because the conventional methods of using them are not enjoyable. They are also difficult to use for many users.

Another problem with the conventional condoms and many prophylactic devices is that they are not attractive to users and do not stimulate interests in users for using them.

A further problem with conventional prophylactic devices is that they are not easily adapted for use in a wide variety of sexual activities.

Yet another problem with conventional prophylactic devices is that they often have to be discarded after one use.

An additional problem with the conventional condoms and their use is that a user has to handle the condom during use which creates risks of contaminating the condom, and thus indirectly infecting a user.

Accordingly, there is a need for a prophylactic device and a method of using condom, which can overcome one or more problems discussed above.

SUMMARY OF THE INVENTION

In accordance with an aspect of the invention, there is provided a method of using a condom which includes covering a penis or prosthesis with a condom. A loose-fitting portion of the condom loosely covers a shaft portion of the penis or prosthesis. The loose-fitting portion has a first end and an opposite second end. The method further includes rotating the first end of the loose-fitting portion of the condom, while holding the second end or rotating the second end in an opposite direction, to twist the loose-fitting portion into a twisted state in which the loose-fitting portion closely covers the shaft portion. The loose-fitting portion of the condom is then secured over the shaft in the twisted state.

In accordance with another aspect of the invention, there is provided an external penile prosthesis. The prosthesis includes a generally tubular body portion extending about a central axis and having opposite first and second open ends for receiving the shaft of a penis therein, and a head portion attached to the first end of the body portion for covering the glans of the penis. The head portion extends along the central axis and is rotatable thereabout.

In accordance with a further aspect of the invention, there is provided an external penile prosthesis, which includes a generally tubular body portion extending about a central axis and having opposite first and second open ends for receiving the shaft of a penis therein, and a head portion attached to the first end of the body portion for covering the glans of the penis. The head portion includes a plurality of flaps. Each flap has a proximal end swingably attached to the body portion and a distal free end. The flaps are swingable about an edge of the first end of the body portion between a closed position and an open position. In the open position, the free ends of the flaps define an opening, and in the closed position, the opening is at least partially closed.

In accordance with another aspect of the invention, there is provided a combination including any one of the prostheses described in the previous two paragraphs and a loose-fitting condom. The condom has a flexible sheath. The sheath has a closed end and an open end. The open end defines an opening for reception of a shaft having a central axis. The shaft is the penis of the user or the prosthesis. The sheath has a loose-fitting portion sized for loosely covering the shaft. The combination may further include a holder for holding the loose-fitting condom in a twisted position in which the sheath is twisted such that the loose-fitting portion of the sheath closely covers the shaft. The holder has an aperture sized for reception and engagement with the sheath over the shaft.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

FIGS. 5A and 5B to 20A and 20B are respectively side and rear elevation views of respective condoms;

FIG. 26A is a front elevation view of another condom holder;

FIG. 26B is a side cross-sectional view of the holder of FIG. 26A along the line B;

FIG. 27A is a front elevation view of an elastic collar;

FIG. 27B is a side cross-sectional view of the collar of FIG. 27A along the line B;

FIG. 31 is a side elevation view of a combination of a condom and the collar of FIG. 27A in use;

FIG. 32A is a front elevation view of an extension cap;

FIG. 32B is a side cross-sectional view of the cap of FIG. 32A along the line B;

FIG. 32C is a side cross-sectional view of the cap of FIG. 32B in a folded position;

FIGS. 40A and 40B are respectively rear and front elevation views of a condom package;

FIG. 40C is a side cross-sectional view of the package of FIG. 40A along the line C;

FIGS. 40D and 40E are side cross-sectional views of the package of FIG. 40A in use;

FIGS. 41A and 41B are respectively rear and front elevation views of another condom package;

FIG. 41C is a side cross-sectional view of the package of FIG. 41A along the line C;

FIGS. 41D and 41E are side cross-sectional views of the package of FIG. 41A in use;

FIGS. 42A and 42B are respectively rear and front elevation views of a further condom package;

FIG. 42C is a side cross-sectional view of the package of FIG. 42A along the line C;

FIGS. 42D and 42E are side cross-sectional views of the package of FIG. 42A in use;

FIGS. 43A and 43B are respectively rear and front elevation views of another condom package;

FIG. 43C is a side cross-sectional view of the package of FIG. 43A along the line C;

FIGS. 43D and 43E are side cross-sectional views of the package of FIG. 43A in use;

FIG. 55A is a front elevation view of a massager;

FIG. 55B is a side elevation view of the massager of FIG. 55A;

FIG. 56A is a front elevation view of a combination of the massager of FIG. 55A and a condom holder;

FIG. 56B is a side elevation views of the combination of FIG. 56A;

FIG. 56C is a side elevation view of the combination of FIG. 56A in a different position;

FIG. 57 is a front elevation view of another massager;

FIG. 64A is a rear elevation view of a combination including a prosthesis and two condoms;

FIG. 64B is a cross-sectional view of the combination of FIG. 64A along the line B;

FIG. 64C is a front elevation view of the combination of FIG. 64A;

FIG. 65 is a rear elevation view of the prosthesis in FIG. 64A in a flattened position;

FIG. 66 is a side cross-sectional view of a combination including a prosthesis and two condoms;

FIG. 67A is a rear elevation view of a combination including a prosthesis and two condoms;

FIG. 67B is a cross-sectional view of the combination of FIG. 67A along the line B;

FIG. 67C is a rear elevation view of the prosthesis in FIG. 67A in a flattened position;

FIG. 67D is a cross-sectional view of the combination of FIG. 67B in a different arrangement;

FIG. 68 is a side cross-sectional view of a combination including the prosthesis of FIG. 60;

FIG. 73A is a rear elevation view of a prosthesis;

FIG. 73B is a side cross-sectional view of a combination including the prosthesis of FIG. 73A;

FIG. 73C is a rear elevation view of the prosthesis of FIG. 73A in a flattened position;

FIG. 73D is a side cross-sectional view of the prosthesis of FIG. 73C;

FIG. 74 is a side cross-sectional view of a combination including two prostheses;

FIG. 75A is a front elevation view of a prosthesis;

FIG. 75B is a cross-sectional view of the prosthesis of FIG. 75A along the line B;

FIG. 76A is a rear elevation view of a package including a prosthesis;

FIGS. 76B and 76C are cross-sectional views of the combination of FIG. 76A along the line B, respectively in retracted and extended positions;

DETAILED DESCRIPTION

An exemplary embodiment of the present invention relates to a method of using a loose-fitting condom. The method can be conveniently practised with a device described below. For example, the method can be practised with the combination of a loose-fitting condom and a condom holder.

Figure 1A:
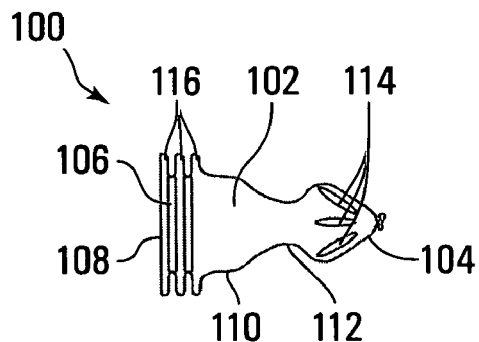
FIGS. 1A and 1B are respectively side and rear elevation views of a condom.
Figure 1B:
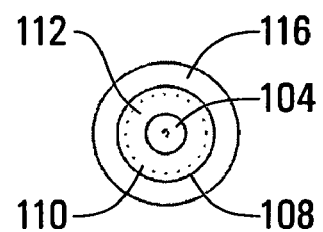

An exemplary loose-fitting condom is illustrated in FIGS. 1A and 1B. Condom 100 has a flexible sheath 102 with a closed (front) end 104 and an open (rear) end 106 for reception of a user's penis or an external penile prosthesis (not shown, but see below and FIG. 4) through an opening 108. Closed end 104 may be tapered and thickened. Sheath 102 may be elastic. Sheath 102 has a loose-fitting portion 110 sized for loosely covering a shaft portion of the penis or the prosthesis. Condom 100 has a non-loose-fitting, neck portion 112 between loose-fitting portion 110 and closed end 104, which has a size for tightly fitting over an erected penis or a prosthesis. The tubular portion of sheath 102 may have a thickness from about 0.01 mm to about 2 mm. Neck portion 112 may be thicker than loose-fitting portion 110. A number of projections 114 are formed on the external wall at closed end 104, extending outwardly, the use of which will become apparent below. In different embodiments, projections 114 can be conical projections or longitudinal ridges formed on the interior or exterior surfaces near or at closed end 104. Condom 100 also has a number of flared lips 116 at open end 106, flaring radially outward for attaching to or housing other components which will be described below. While condom 100 has three flared lips 116, in alternative embodiments, the number of flared lips can be more or less. The thickness of a flared lip 116 may be similar or thicker than the wall thickness of sheath 102.

Condom 100 can be made of any suitable material and in any suitable manner as can be understood by persons skilled in the art. For example, a material for making conventional condoms may be used. The condom may be made of a prophylactic material. The material may be flexible or elastic.

A surface of condom 100 may be coated or otherwise treated with a medicament, a lubricant, a contraceptive material, or any combination thereof.

Figure 2A:
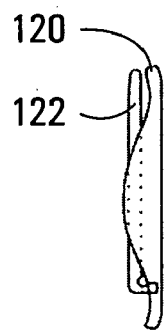
FIG. 2A is a side elevation view of a condom holder with a clamp in a folded position.
Figure 2B:
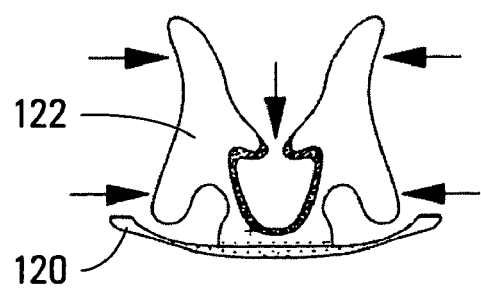
FIG. 2B is a top plan view of the holder of FIG. 2A with the clamp in an extended position.

An exemplary condom holder 120 is illustrated in FIGS. 2A and 2B. Holder 120 can be attached to condom 100 in any suitable manner, such as to a flared lip 116 at open end 106.

Holder 120 can have a clamp 122 which is foldable when not in use, as shown in FIG. 2A. As shown in FIG. 2B, clamp 122 defines a generally C-shaped notch for receiving a user's body part (not shown) when clamp 122 is unfolded or extended. Thus, clamp 122 can be used to attach holder 120, and hence the condom attached to holder 120, to a user's body during use.

Figure 2C:
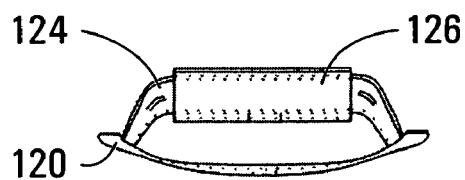
FIG. 2C is a top plan view of the holder of FIG. 2A with a band.

As illustrated in FIG. 2C, in an alternative embodiment, clamp 122 may be replaced with a band 124. Band 124 can be elastic. A pad 126 may be attached to band 124, the use of which will become apparent below. Pad 126 may be made of a firm material.

An adhesive material may be applied to a surface of holder 120 for attaching it to a user.

One or more soft absorbent sealing pads (not shown) may also be attached to holder 120, such as near its outer periphery, for attaching the holder to a user.

The side of holder 120 that is in contact with the user during use may be contoured such that the contoured surface is in substantial conformity with the surface of the user's body it contacts.

Holder 120 may be made of any suitable material and may have any desirable shape. For example, holder 120 may be rigid, semi-rigid, or spongy. The material may also be absorbent. A person of skill in the art can readily construct a suitable holder 120.

Figure 3A:
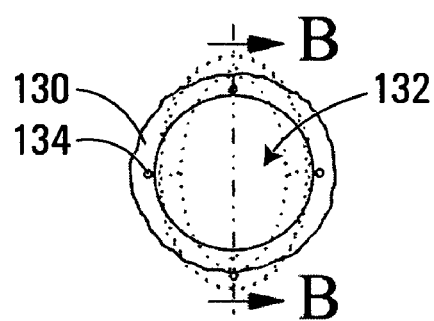
FIG. 3A is a front elevation view of a retainer.
Figure 3B:
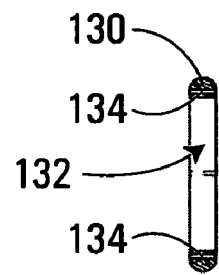
FIG. 3B is a side cross-sectional view of the retainer of FIG. 3A along the line B.

An exemplary retainer ring 130 is illustrated in FIGS. 3A and 3B. Retainer ring 130 is generally ring-shaped and has a central aperture 132 sized for reception and engagement of sheath 102 of condom 100 over a penis or prosthesis. Retainer ring 130 has a number of holes 134, the use of which will be described below. As depicted, the distance from the outer periphery of ring 130 to the centre may vary.

Retainer ring 130 may be made of any suitable material and have any suitable shape and size. For example, ring 130 may be elastic and can be deformed such as shown by the ghost lines in FIG. 3A. A suitable retainer ring can be readily constructed by a person skilled in the art.

In use, condom 100 can be used to cover a user's penis or a prosthesis, as described below in accordance with the exemplary method of using a condom.

Figure 4:
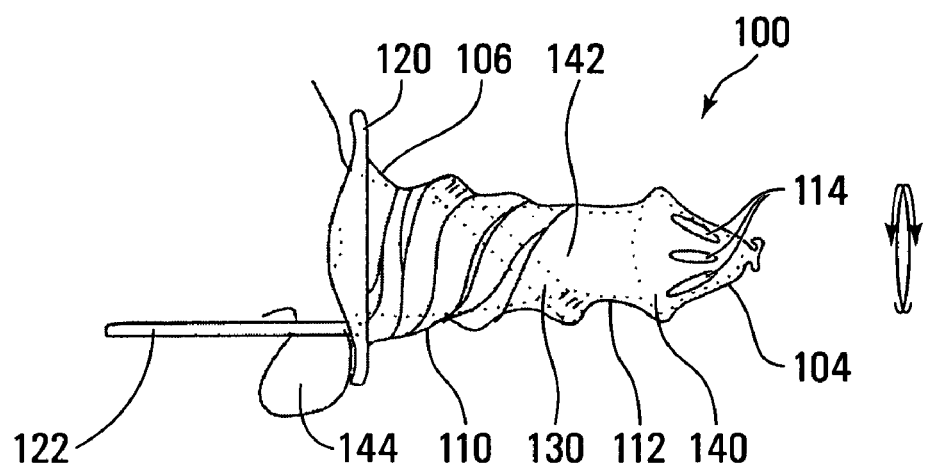
FIG. 4 is a side elevation view of the combination of the condom of FIG. 1A, holder of FIG. 2A and retainer of FIG. 3A in use.

As illustrated in FIG. 4, condom 100 is attached to holder 120. Condom 110 covers a penis 140 (shown in ghost line) in a twisted state, in which loose-fitting portion 110 of condom 100 is twisted and closely covers penis 140. To do so, penis 140 is inserted into condom 100 through the opening at open end 106. Initially, loose-fitting portion 110 loosely covers a shaft portion 142 of penis 140. One end (e.g. the closed or front end 104) of sheath 102 can be rotated about a central axis of penis 140 while the other end (e.g., the rear and closed end 106) of sheath 102 is held in place or rotated in an opposite direction (as indicated by the arrows), to twist loose-fitting portion 110 into the twisted state. Projections 114 and holder 120 can be used to facilitate the twisting motion. Loose-fitting portion 110 is then secured over penis shaft 122 in this twisted state, such as with the use of holder 120, which can be attached to a user's body. As shown, open end 106 of condom 100 is attached to holder 120 which can be clamped to the user's body. For instance, clamp 122 can be clamped around the user's scrotum 144, between the thighs and against the perineum. The user may squeeze clamp 122 lightly when needed to keep holder 120 in place for holding condom 100.

As can be appreciated, the loose-fitting portion of the condom can also be secured, at least in part, using a user's body. For example, the condom may be held in position with the fingers of a user. When the condom has a tight-fitting portion, the friction between the tight-fitting portion and the shaft may be sufficient to prevent unintentional rotation of the tight-fitting portion, thus keeping the condom in the twisted state.

Ring 130 is placed inside condom 100 (shown in ghost line) for stimulation purposes. However, as will be further explained below, retainer ring 130 may also be placed outside sheath 102 for holding condom 100 in the twisted state.

Conveniently, projections 114 may also provide stimulation to the user or the user's partner. Holder 120 also makes it easier to handle condom 100. For example, with holder 120, direct contact between sheath 102 and a user during handling of condom 100 can be reduced or avoided, as can be understood by a person skilled in the art.

As can be appreciated, by twisting the condom, it is possible to adjust the length and width of the condom, and to release air trapped at the front end of the condom. When the loose-fitting portion is twisted, it fits better with the contour of the penis or the prosthesis, which may be preferred by some users.

The use of retainer ring 130 is optional. It may be used to create different twisting forms of condom 100, such as by placing it in different positions over the penis. The size of retainer ring 130 may also vary for this purpose. When the twisting form or shape of the condom is varied, the user may experience different sensations during use. Since the twisting form/shape of the condom can vary, it may create a mysterious effect and thus increase the user's enjoyment or pleasure in using it. The mysterious effect can also be created by placing in condom 100 a different object, such as a prefabricated jacket with un-even surfaces. The jacket may be made of any suitable material including paper.

While not shown in FIG. 4, clamp 122 may be replaced by band 124 and pad 126. Pad 126 may be placed behind the scrotum 144 for securing and stabilizing holder 120. For a female user, clamp 122 may be replaced with a band (not shown) which can be tied around the user's waist.

As can be understood, the twisting method of using condom described above can also be practised when the user wears an external penile prosthesis over his penis. The prosthesis can be covered with the loose-fitting condom. The shaft portion of the prosthesis may be covered by the loose-fitting portion of the condom similarly to the penis shaft. A prosthesis disclosed herein can be advantageously used, as will be further described below.

Other types of loose-fitting condoms can also be used. Exemplary alternative condoms are illustrated in FIGS. 5A and 5B to 20A and 20B. As can be seen, the condoms can have various sizes and shapes. For example, the opening at the open end of the condom may have a relatively large diameter, such as larger than that of the shaft portion to be received therein. The large opening can be large enough for receiving the scrotum of a user. Condoms with large openings are shown in FIGS. 1A and 1B, and 5A and 5B to 14A and 14B. Optionally, the condom may have a pocket (not shown) near the open end for receiving and retaining a scrotum therein during use, as will be further described below. Alternatively, the opening at the open end may have a medium diameter, such as similar to that of the shaft portion. Condoms with medium openings are shown in FIGS. 15A and 15B to 18A and 18B. The opening at the open end may also be relatively small, such as substantially smaller than that of the shaft portion. Condoms with small openings are shown in FIGS. 19A, 19B, 20A and 20B. For example, the small opening, such as in each of condoms 290 and 300, may have a diameter of about 0.5 mm.

As can be seen, the open end of a condom with a medium or small opening can have a bottle-neck-like shape, as defined by the flared-lip portion. The bottle-neck portion of the condom sheath, which is adjacent or at the open end, can fit closely over a base portion of the shaft of the penis or prosthesis. The bottle-neck portion should be elastic and the opening may have an initial or natural diameter substantially smaller than that of the base portion of the shaft so that the bottle neck-portion can be in sealing and frictional engagement with the base portion of the shaft.

In some embodiments, the initial diameter of an opening at a flared lip can be, for example, more than about 0.3 in.

The bottle-neck portion may be of different uses. For example, it may be used for storing the loose-fitting and front portions of the condom when not in use. It may be used to prevent fluid leakage during use. When used by a female user, it may serve as a soft guard, for example when the female user has recently given birth. It may also help securing the condom in place during use. With the bottle-neck having a small opening, when a shaft is inserted into the condom, the bottle-neck can expand radially outwardly from the relaxed position and thus a large radial pressure can be exerted on the condom and the shaft received in the condom, for holding the condom in place.

Further, as in condom 100, a condom sheath may have a non-loose-fitting portion, or an elastic neck portion between the loose-fitting portion and the closed end, such as shown in FIGS. 1A, 8A, 9A, 12A, 13A, 14A, 17A, 19A, and 20A. The neck portion can be sized for close-fit over and frictional engagement with a head portion of a penis or prosthesis.

As shown in some of the figures, the sheath of a condom may have a portion which has varying internal and/or external diameters for increased stimulation of a user during use.

In different condoms, the number of flared lips can vary. Different flared lips may have different thickness, such as shown in FIGS. 6A, 15A and 16A. A flared lip may be thicker than a tubular portion of the sheath adjacent the flared lip.

FIGS. 16A and 16B illustrate a dual-condom 260, where two condom sheaths 262 and 264 are integrally formed on a same backing sheet. The open ends of sheaths 262 and 264 are positioned close to each other. As can be understood, condom 260 is suitable for simultaneous vaginal and anal use. During use, sheath 262 (or 264) may be twisted as described above.

Figure 21:
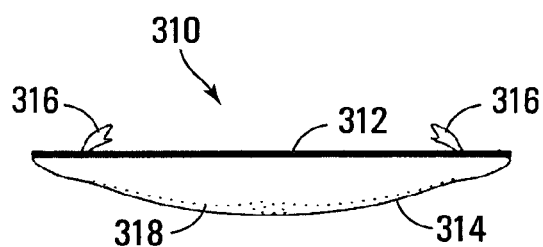
FIGS. 21 to 25 are top plan views of respective condom holders.

FIG. 21 illustrates an alternative condom holder 310, which has a flat back side 312 and a curved front side 314. Elastic bands 316 are attached to back side 312 for securing holder 310 in place during use. Bands 316 can be attached to flange 310 with a fastener such as a clamp or an adhesive material. An adhesive can be applied to backside 312 for attaching holder 310 to a user. The adhesive can be a medical adhesive. A condom 318 (shown in ghost line) can be attached to holder 310.

Figure 22:
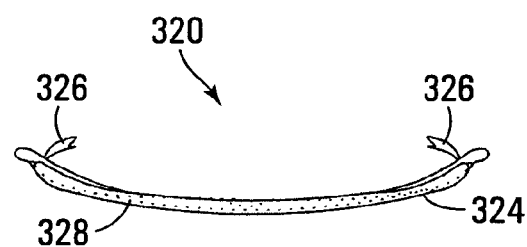

FIG. 22 illustrates another holder 320, which has a frame 322 and an elastic front wall 324. Elastic bands 326 are attached to frame 322. A condom 328 (shown in ghost line)

can be attached to holder 320. Frame 322 and front wall 324 are curved to conform to the body of a user.

Figure 23:
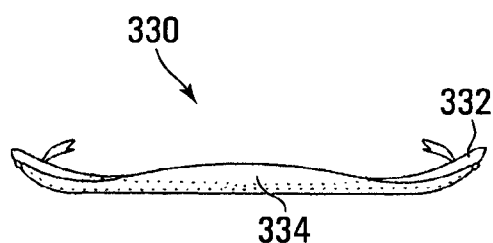

FIG. 23 illustrates a holder 330, which is a variation of holder 320. Holder 330 also has a frame 332 and an elastic front wall 334, but their central portions are flat, instead of curved.

Figure 24:
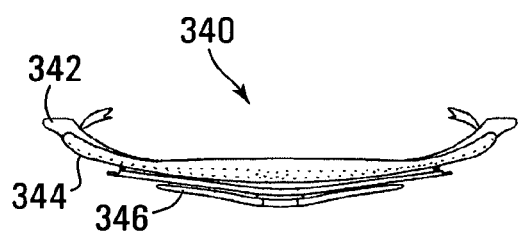

FIG. 24 illustrates a holder 340, which is also a variation of holder 320. Holder 340 has a frame 342, a front wall 344 and a constriction ring 346 attached to front wall 344. The structures, use and benefits of constriction rings will be described below.

Figure 25:
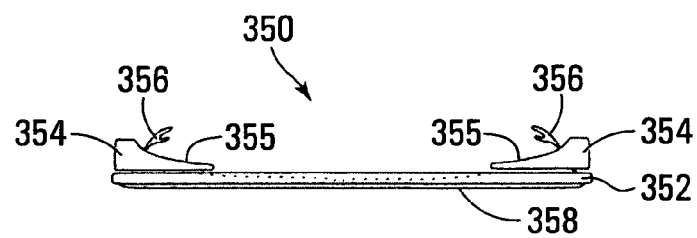

FIG. 25 illustrates a holder 350 which has a flat frame 352 and attachment members 354 attached to frame 352. Each member 354 has a curved surface 355 for conforming to the body of a user. Elastic bands 356 and an elastic front wall 358 are respectively attached to frame 352.

FIGS. 26A and 26B illustrate a further alternative condom holder, which includes a frame or flange 360. Flange 360 may have a generally disk-like shape or hemispherical shape. Flange 360 has a central opening or aperture 362 sized for receiving a condom over a penis or prosthesis. Aperture 362 typically has a diameter larger than the diameter of the shaft to be received therein. For example, the central opening may have a size of about 1.5 inches to 15 inches. Bands or straps 364 are attached to flange 360 for securing or holding the flange, and therefore the condom attached to it, in place. Straps 364 can be an elastic band. Straps 364 may be attached to flange 360 with a fastener such as a clamp or an adhesive material.

In different embodiments, different straps can be used. For example, the strap can be an elastic band. A pad (not shown) may be attached to straps 364 for being placed behind the scrotum of the user so as to secure the condom in place, similar to band 124 and pad 126 shown in FIG. 2C.

One or more soft absorbent sealing pads may also be attached to flange 364, such as adjacent an outer periphery of the flange, for attaching the flange to a user.

A side of flange 360 that is in contact with the user during use may be contoured such that the contoured surface is in substantial conformity with the surface of the user's body it contacts.

Flange 360 can also be used for handling a condom attached to it. To facilitate handling, a radially outward-facing surface adjacent the outer periphery of flange 360, such as surface 366, may be slip-resistant. The surface may be made of or coated with a non-slippery material, or may be roughened.

Flange 360 may be made of a semi-rigid or rigid material and can be readily constructed by a person skilled in the art.

As now can be understood, straps 364 are optional and may be omitted or replaced by another securing member such as a hook, a clamp, a loop, a ring, or an adhesive tape. The adhesive tape can be a medical adhesive tape. Flange 360 may also have an adhesive surface for attachment to the user.

FIGS. 27A and 27B illustrate a further alternative condom holder, a collar 370. Collar 370 is elastic and has an aperture 372 sized for reception and engagement with sheath 102 of condom 100 over a penis or a prosthesis. Small openings 374 are provided near the outer peripheral of collar 370 for releasing trapped air.

As can be appreciated, collar 370 and retainer ring 130 can be similarly structured. In use, one of them may be substituted by the other. The depicted collar 370 or retainer ring 130 is generally ring-shaped, but they may have a different shape.

Figure 28:
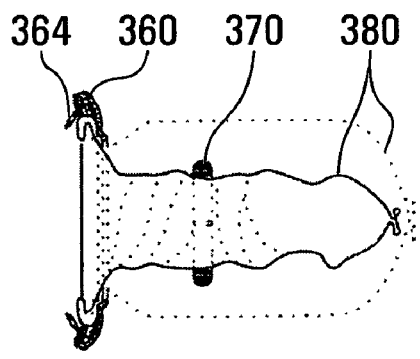
FIG. 28 is a side, partial cross-sectional view of a combination of a condom, the holder of FIG. 26A, and the collar of FIG. 27A in use.

Collar 370 may be placed outside a condom to hold the condom in a twisted state, as illustrated in FIG. 28.

As illustrated in FIG. 28, a condom 380 can be twisted from a loose state (shown in the ghost outline) into a twisted state (shown in solid line) and closely cover a shaft (not shown). As shown (in dotted line), condom 380 can be twisted into a spiral shape. Collar 370 is placed over condom 380 in its twisted state such that a portion of condom 380 is received in the central aperture of collar 370 so as to hold condom 380 in the twisted state. The aperture can be sized such that collar 370 abuts condom 380 against the shaft to retain condom 380 in the twisted state by friction. Collar 370 may be placed close to the front end or the rear end, or at the middle of condom 380. As can be understood, when collar 370 is placed at the middle, condom 380 may be twisted into a twin-spiral shape, such as by rotating collar 370, or twisting both ends of condom 380 in the same direction.

Condom 380 can be attached to flange 360. Flange 360 can be strapped to a user with straps 364.

Figure 29:
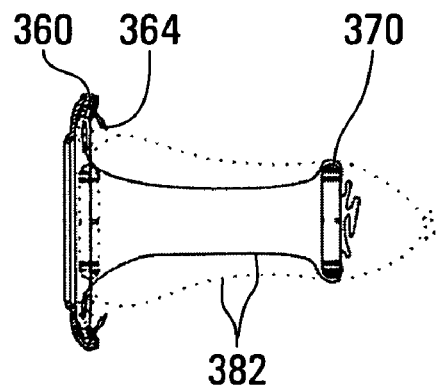
FIG. 29 is a side, partial cross-sectional view of a variation of the combination of FIG. 28.

As illustrated in FIG. 29, collar 370 may be placed inside a condom 382 for female use. As illustrated, for female use, the orientation of flange 360 may also be reversed so that straps 364 are on the same side as condom 382.

A number of collars with same or different sizes or shapes may be provided. They may be color coded. That is, each collar may have a distinct color for ease of identification or for stimulating user interest.

Figure 30A:
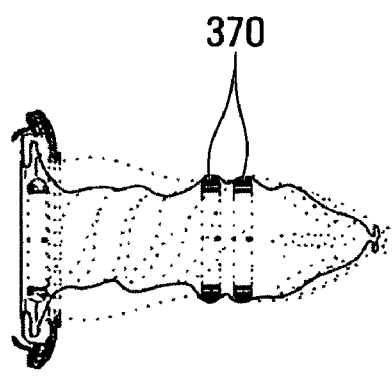
FIGS. 30A and 30B are side, partial cross-sectional views of respective combinations with two or three of the collar of FIG. 27A in use.
Figure 30B:
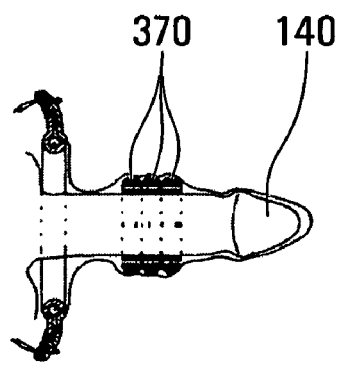

As is apparent, two or more condom holders can be used simultaneously. For example, two or more collars 370 can be used as illustrated in FIGS. 30A and 30B, wherein two or three collars 370 are respectively placed inside a condom and, for example, over penis 140.

As illustrated in FIG. 31, collar 370 can be placed inside a condom 302 in a twisted state, near the open end or at the base portion of the shaft (not shown) received in the condom.

FIGS. 32A to 32C illustrate an extension cap 390 which has a central web 392 defining a central opening 394. It also has a number of foldable, fan-like flaps 396 extending radially from central web 392. Cap 390 has a radially contoured surface. Extension cap 390 is normally in a flat position as shown in FIG. 32B but foldable flaps 396 can be bent or folded towards the central axis, as illustrated in FIG. 32C. Each flap 396 may have a thickened tip 398. Extension cap 390 can be sized so that it can be received within a condom. As can be seen in FIG. 32B, opening 394 can be shaped such that it forms a fluid chamber defined by central web 392 for storing a body fluid discharged by a user during use.

Figure 33:
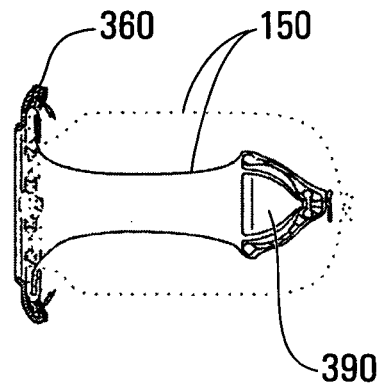
FIG. 33 is a side, partial cross-sectional view of a combination including the cap of FIG. 32A.

In use, extension cap 390 can be placed inside a condom. As illustrated in FIG. 33, cap 390 may be placed inside a condom 150 for expanding and holding condom 150 in a vagina. Extension cap 390 may also be used as a penis extension, for twisting the condom, or for stimulating a user (also see FIGS. 40D and 40E). Conveniently, trapped air can be released through central opening 394. A fluid discharged by a user may be temporarily stored in opening 394.

Figure 34A:
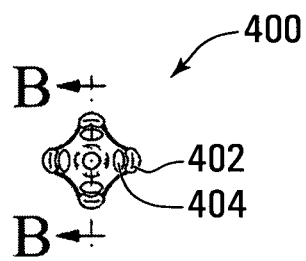
FIG. 34A is a front elevation view of another extension cap.
Figure 34B:
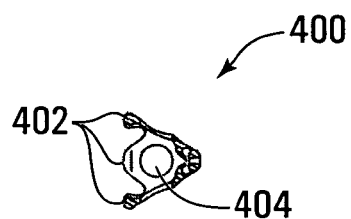
FIG. 34B is a side cross-sectional view of the cap of FIG. 34A along the line B.

FIGS. 34A and 34B illustrate another extension cap 400 which is similar to cap 390 in structure and functionality, but has a naturally tapered shape and projecting lips 402, instead of flaps. Further, each lip 402 has a through hole 404. Each hole 404 may be sized to allow a foreign object, such as a user's finger, to apply pressure on the covered shaft during use. Holes 404 may also be used for releasing trapped air or for trapping discharged bodily fluid.

Figure 35A:
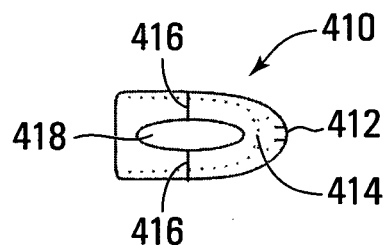
FIG. 35A is a side elevation view of another cap.
Figure 35B:
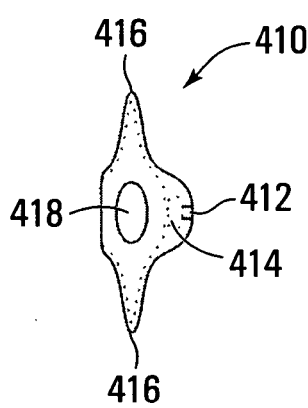
FIG. 35B is a side elevation view of the cap of FIG. 35A in a flattened position.
Figure 35C:
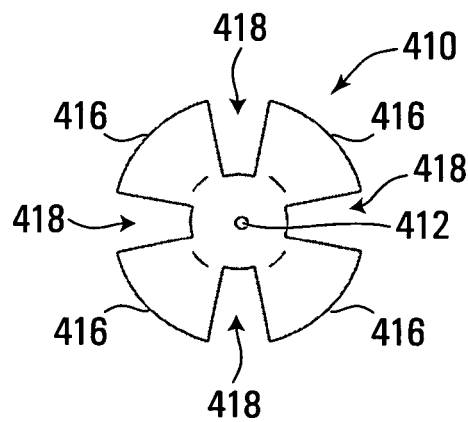
FIG. 35C is a front elevation view of the cap of FIG. 35B.

FIGS. 35A to 35C illustrate yet another cap 410. Cap 410 has a central hole 412 for releasing trapped air, a cavity 414 for trapping semen, weakened portions 416 for easy flattening, and sidewall windows 418 for contacting a covered shaft (not shown) during use. As illustrated in FIG. 35B, cap 410 can be flattened along the weakened portions 416 for easy storage. Cap 410 may be used as a penis extension or finger extension, to retain a condom in a vagina, or even as a prosthesis, as can be understood by a person skilled in the art.

For convenience of use and to stimulate user interest, a number of extension caps, such as caps 390, 400, and 410, may be provided within a condom package. The caps may have different colours. For example, the caps may have different sizes or shapes and are colour-coded, that is, each cap has a distinct colour for identification purposes. For instance, blue and pink colours may be respectively used to indicate that it is for a male user or a female user.

Figure 36A:
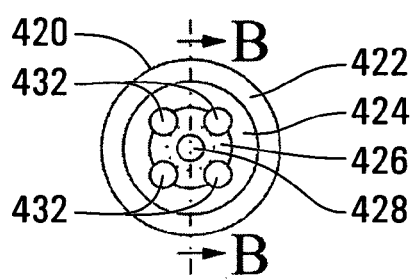
FIG. 36A is a front elevation view of a constriction ring.
Figure 36B:
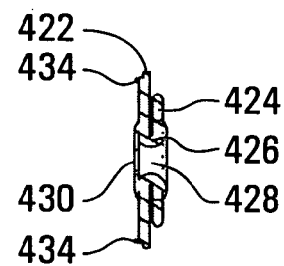
FIG. 36B is a side cross-sectional view of the constriction ring of FIG. 36A along line B.

FIGS. 36A and 36B show a constriction ring 420. Ring 420 has two layers of elastic sheets 422 and 424 at opposite ends, which are joined at a central portion 426. Each layer 422 or 424 may have a thickness of about 1 mm. The total thickness of ring 420 may be about 5 or 7 mm. Ring 420 has a central opening 428 for receiving a penis covered with a condom there through. Opening 428 may have a diameter of about 10 mm. It may also have a narrowed portion 430. The thickness of each layer may gradually increase towards opening 428. Ring 420 is elastic and opening 428 is sized to frictionally engage a condom over a penis received therein. Layer 424 defines four peripheral openings 432 for aiding the handling of ring 420. For example, openings 432 can be sized to allow insertion of a human finger for stretching central opening 426. Layer 422 may have an attachment member 434 for attaching ring 420 to, for example, flange 360 or another holding and handling component, as will be further described below.

A layer, such as layer 424, of constriction ring 420 may have projections (not shown) thereon extending outwardly, for stimulating a female user.

An additional layer of elastic sheet (not shown) may be attached to rear layer 422 near the outer periphery. The additional layer may have a central aperture having a diameter of about 6 mm and have a thickness similar to the thickness of a condom sheath.

Constriction ring 420 can be constructed with any suitable material and in any suitable manner, which will be understood by persons skilled in the art after reviewing this paper.

In use, constriction ring 420 can be placed on a condom covering a penis, for example, in a similar manner as for collar 370 described above. However, the central opening of constriction ring 420 is relatively small and it may be used for maintaining penis erection, delaying premature ejaculation, and holding the condom in place. The use of constriction ring 420 will be further illustrated below.

Figure 37A:
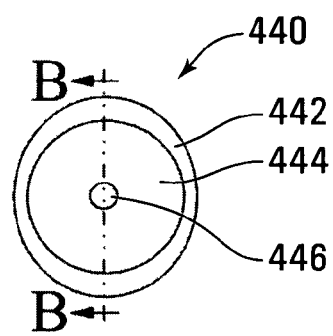
FIG. 37A is a front elevation view of a front frame.
Figure 37B:
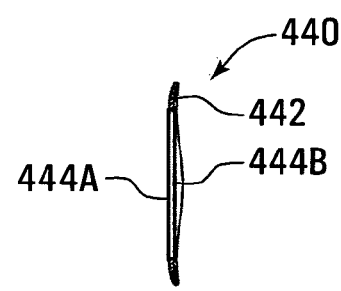
FIG. 37B is a side cross-sectional view of the frame of FIG. 37A along the line B.

FIGS. 37A and 37B illustrate a front frame 440, which can be used in combination with flange 360. Frame 440 has an outer frame 442, front and back elastic sheets 444A and 444B (also collectively or individually referred to as 444). Frame 440 defines a central opening 446. Frame 440 may be attached to flange 360.

The thickness of sheets 444 may be determined depending on the desired radial tension on the perimeter of the penis. The thickness of a sheet 444 may also vary from the perimeter to the center, such as thinner at the center.

In different embodiments, several concentric elastic rings (not shown) of different sizes may be formed on elastic sheets 444.

More than two sheets 444 may be provided, which may also have different central aperture sizes, or have different elasticity. However, it may be advantageous to have two sheets with concentric central apertures of different diameters. For example, one aperture may have a diameter of about 0.5 in and the other may have a diameter of about 0.75 in.

Figure 38A:
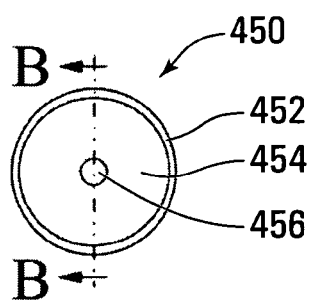
FIG. 38A is a front elevation view of a rear frame.
Figure 38B:
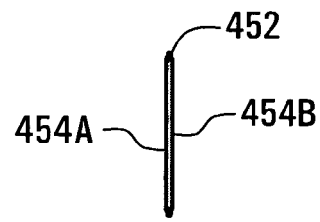
FIG. 38B is a side cross-sectional view of the frame of FIG. 38A along the line B.

FIGS. 38A and 38B illustrate a rear frame 450, which can be used in combination with flange 360. Frame 450 has an outer frame 452, front and back elastic sheets 454A and 454B (also collectively or individually referred to as 454). Frame 450 defines a central opening 456.

Sheets 454 may be similarly to or modified from sheets 444. However, the central apertures may have different sizes. For example, the central apertures of sheets 454 may be larger.

Frames 440 and 450 may be attached to flange 360, respectively on the front and rear sides of flange 360, wherein their central openings 446 and 456 are substantially co-axial. Both central openings 446 and 456 may be sized for frictional engagement with a condom covering a penis received therein.

Constriction ring 420 can also be attached to frame 440 or 450.

Figure 39A:
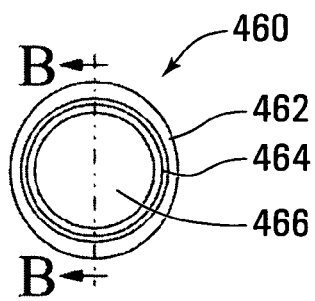
FIG. 39A is a front elevation view of a housing member.
Figure 39B:
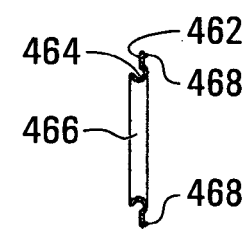
FIG. 39B is a side cross-sectional view of the housing member of FIG. 39A along the line B.

FIGS. 39A and 39B illustrate an annular housing member 460, which can be used in combination with other components described herein including flange 360. Housing member 460 has a generally ring-shaped outer frame 462, which defines a groove 464 and a central opening 466. An attachment member 468 is provided on outer frame 462 for attaching housing member 460 to flange 360. Housing member 460 may be attached to flange 360 so that their central openings are substantially co-axial.

Housing member 460 can be made of any suitable materials and in a suitable manner readily understood by persons skilled in the art.

Groove 464 may be used for storing a condom prior to use and for holding the condom during use. For example, a flared lip or a rim at the open end of a condom may be received in groove 464. The condom may also be rolled-up and substantially stored in groove 464 as can be readily appreciated by persons skilled in the art.

The use of frames 440 and 450 and housing member 460 will be further described below.

An exemplary embodiment of the present invention is a condom package 470 shown in FIGS. 40A to 40C.

Package 470 includes a rear shielding sheet 472 and a front shielding sheet 474. Sheet 472 has an opening 473. Sheet 472 can be double-folded while sheet 474 can be a single layer. A condom combination is enclosed in package 470 between sheets 472 and 474. Components of the combination may vary. As depicted, the combination includes a flange 360, a condom 220A attached to flange 360 at its open end, and a cap 390. An optional second condom (not shown but see FIG. 40D) may be included.

Sheets 472 and 474 can be flexible or elastic. They shield the condom combination from contamination or damage before use. Sheet 472 may be sufficiently large for easy handling and for covering an adhesive portion at backside of flange 360.

During use, sheets 472 (if it has no opening) and 474 can be pierced to allow a penis or prosthesis to go through. Sheet 472 may be removed during use, for example, to expose the adhesive portion of flange 360 so that it can be attached to a user.

While shielding sheets 472 and 474 may be removed during use, they provide protective and hygienic packaging, and help easy handling and application of the condom. For example, shielding sheet 472 can help attaching flange 360 to the user's body, such as by pulling the tip of each end of the sheet to expose the adhesive on the back surface of the flange.

As shown in FIGS. 40D and 40E, after condom 220A is put on a penis (not shown), condom 220A can be twisted into a twisted state as described above. As shown by the dotted lines, condom 220A can be twisted to form wrinkles. An additional holder such as front frame 440 may be placed over the twisted condom 220A for holding condom 220A in the twisted state.

As shown in FIG. 40D, an additional condom 220B may be provided to cover condom 220A.

FIGS. 41A to 41C illustrate another package 480. Again, a condom combination is enclosed between shielding sheets 482 and 484. A condom 486 and two caps 390 are provided, one inside and one outside condom 486. Instead of a flange, condom 486 is attached to two separated holding and handling segments 488, adjacent the opening at its open end.

In use, sheet 484 may be removed as shown in FIGS. 41D and 41E. A penis (not shown for clarity) may be inserted into condom 486 from the left hand side as shown in FIG. 41D, through sheet 482 (not shown). Alternatively, the penis may be inserted into condom 486 from the right hand side, as shown in FIG. 41E. In either case, holding and handling segments 488 may be attached to a user for holding condom 486. Depending on the direction of insertion, the users may choose to whom the segments will be attached. When used as a male condom, condom 486 may be twisted as shown by the dotted lines in FIG. 41D. Condom 486 may also be used as a female condom as shown in FIG. 41E.

FIGS. 42A to 42C illustrate a further condom package 490. It has shielding sheets 492 and 494 enclosing a dual condom 496 which has two sheaths 498 and 499. Shielding sheet 492 may be used as a pulling tab. The open ends of sheaths 498 and 499 are near each other and may be spaced differently for different uses and applications. The closed ends of sheaths 498 and 499 can extend towards the same or opposite directions. Package 490 also includes three caps 390.

In use, sheaths 498 and 499 can be used simultaneously, for example, as shown in FIGS. 42D and 42E, or one after another. A person skilled in the art can readily understand the use and operation of condom 496. For example, the two sheaths can be used one after the other for two separate sexual activities including oral sex, in quick secession. The sheaths can be used hygienically. The top condom sheath 498 can be used either by a female or a male user, and the bottom sheath 499 can be used as an anal condom. The three caps 390 may have different colors for indicating their use. For example, the two caps on the left-hand side in FIG. 42C may be pink and the cap on the top-right may be blue.

FIGS. 43A to 43C illustrate a further condom package 500. It has shielding sheets 502 and 504 enclosing a single-sheath condom 506, and two caps 390. Condom 506 is attached to a flange 508. Flange 508 is made of a flexible, bendable material. A side 510 of flange 508 is of a soft, absorbent material and its surface is adhesive. Flange 508 may be suitable for attaching to a male or female user.

In use, side 510 may face a female user (not shown) as shown in FIG. 43D, or face a male user (not shown) as shown in FIG. 43E. In either case, flange 508 may be bent, as shown in ghost lines, to conform to the user's body shape.

Figure 44A:
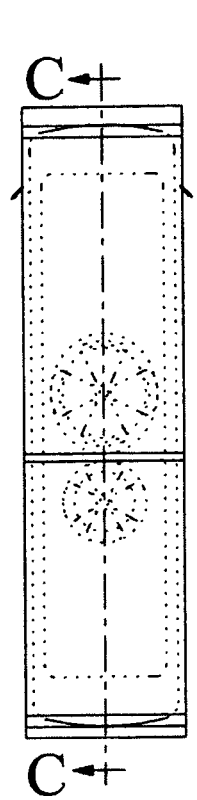
FIGS. 44A and 44B are respectively front and rear elevation views of a condom package.
Figure 44B:
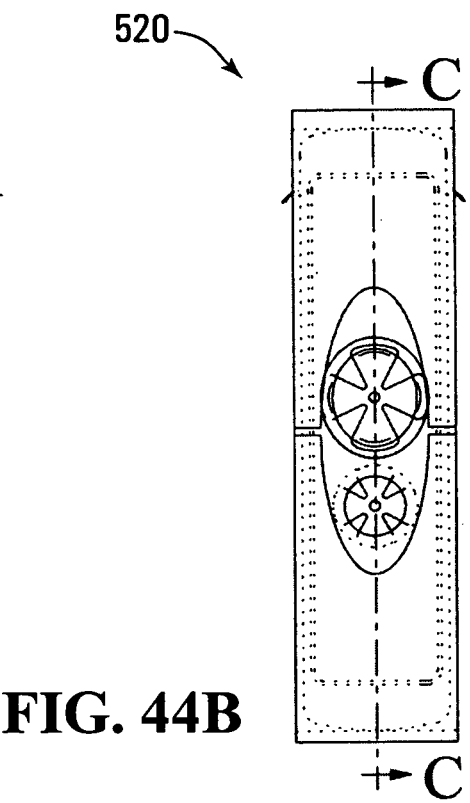
Figure 44C:
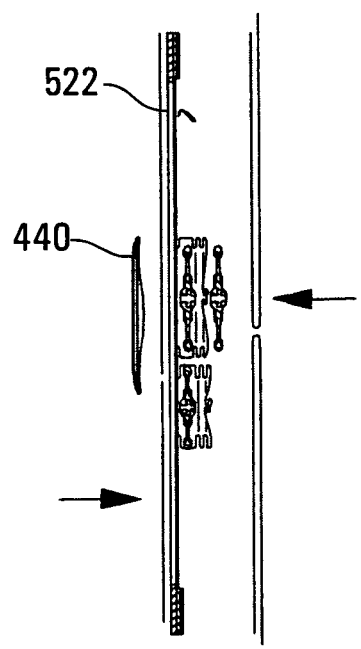
FIG. 44C is a side cross-sectional view of the package of FIG. 44A along the line C.
Figure 44D:
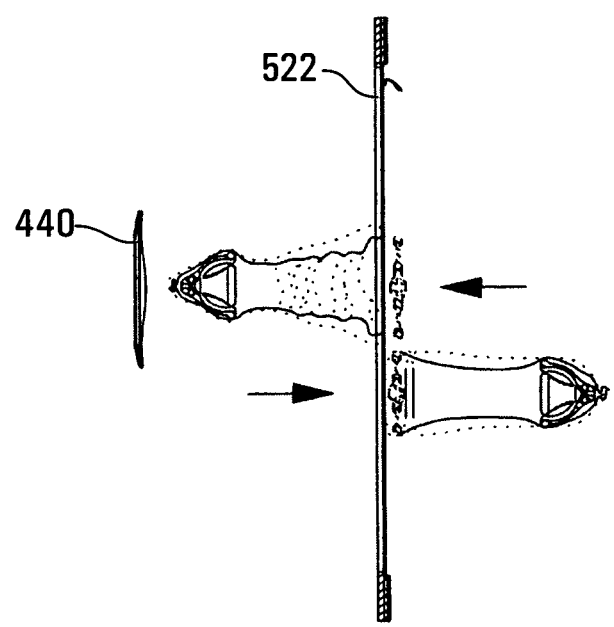
FIGS. 44D and 44E are side cross-sectional views of the package of FIG. 44A in use.
Figure 44E:
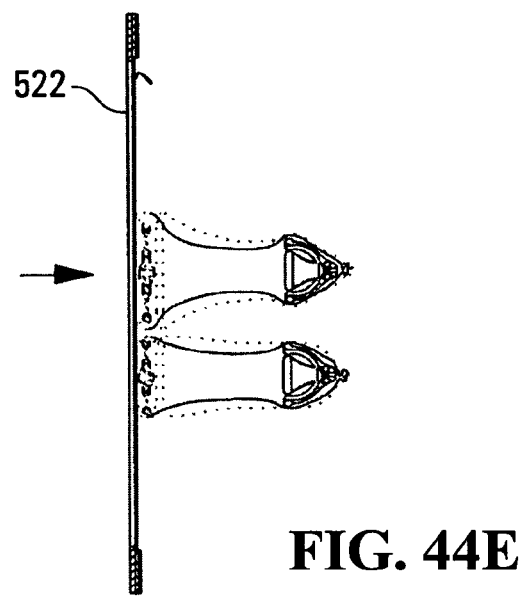
Figure 44F:
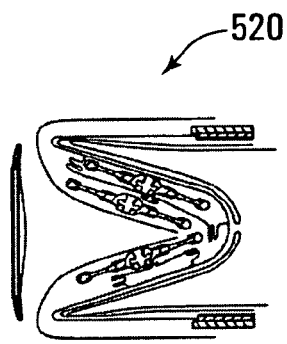
FIGS. 44F to 44H are side cross-sectional views of the package of FIG. 44A in storage.
Figure 44G:
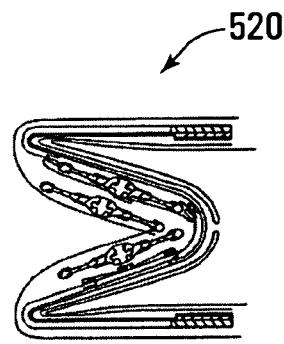
Figure 44H:
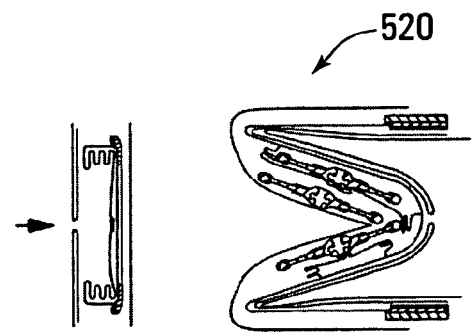
Figure 45:
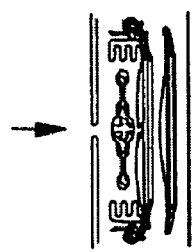
FIGS. 45 to 50 are respectively side cross-sectional views of different condom packages.
Figure 46:
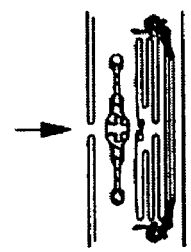
Figure 47:
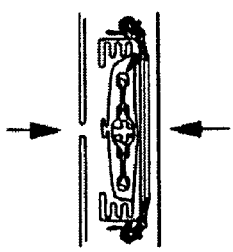
Figure 48:
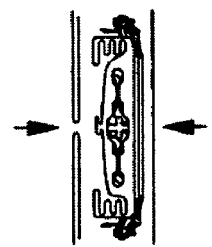
Figure 49:
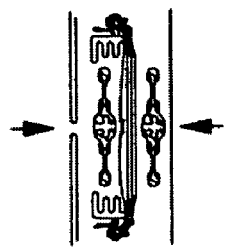
Figure 50:
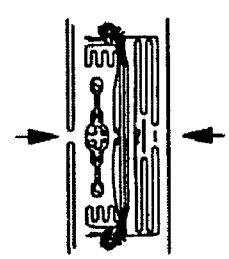

FIGS. 44A to 44C illustrate another dual condom package 520 which has a dual condom 522 and a frame 440. FIGS. 44D and 44E illustrate the use of package 520.

As can be understood, a condom may be stored in rolled-up, folded or collapsed state before use. However, rolled-up condoms may not be convenient to use, especially if it is loose-fitting. It may take time to unroll the condom. Inexperienced users may have difficulties unrolling the condom with a single hand or when in a rush. It may be desirable that the condom is stored in a collapsed or folded state before use so that it can be easily opened for use.

As illustrated in FIGS. 44E to 44H, package 520 can be easily folded in different manners during storage. It is not necessary to roll-up condom 522. Thus, package 520 is convenient to use.

As can be appreciated, a package can contain different components depending on the intended user and use. Some example combinations are shown in FIGS. 45 to 50.

Figure 51A:
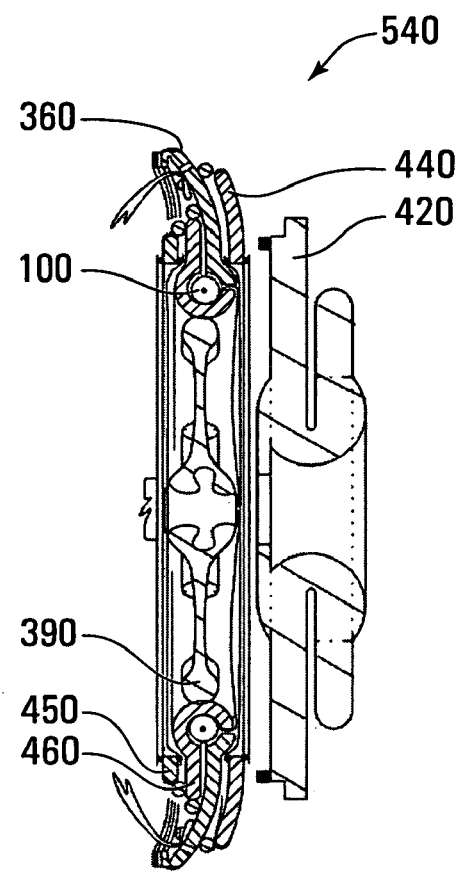
FIG. 51A is a side cross-sectional view of a condom package.
Figure 51B:
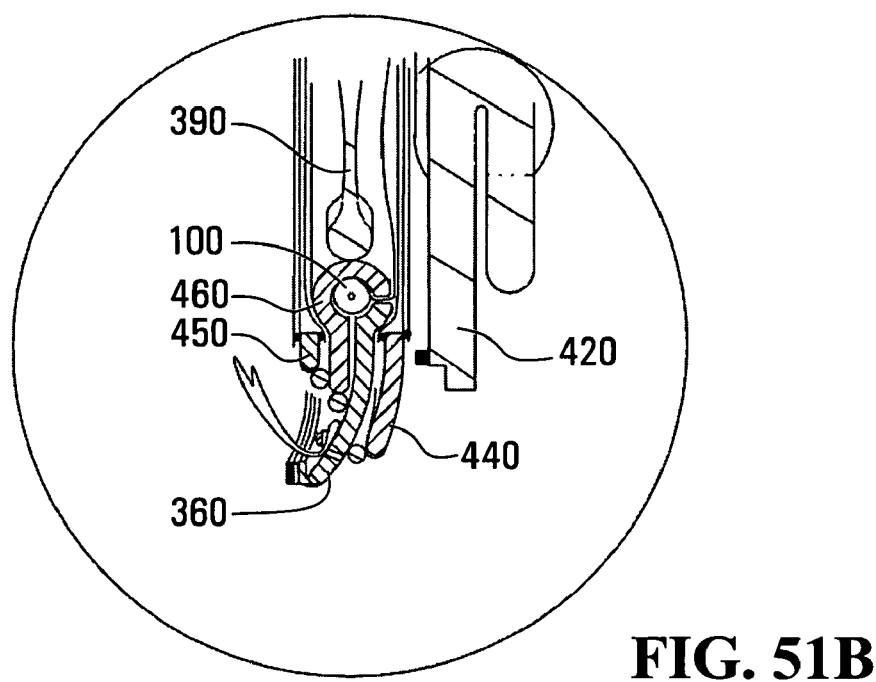
FIG. 51B is a magnified view of a portion of the package of FIG. 51A.

FIGS. 51A and 51B illustrate another exemplary package 540, which includes an assembly of flange 360, front and rear frames 440 and 450, housing member 460, foldable cap 390, constriction ring 420, and a condom such as condom 100 stored in housing member 460. The relative positions of the components can be best viewed in FIG. 51B. The use of package 540 can be readily understood by persons skilled in the art after reviewing this paper.

As can be appreciated, the condoms and combinations disclosed herein can be used by both men and women, and may be used either for intercourse or oral sex.

Figure 52:
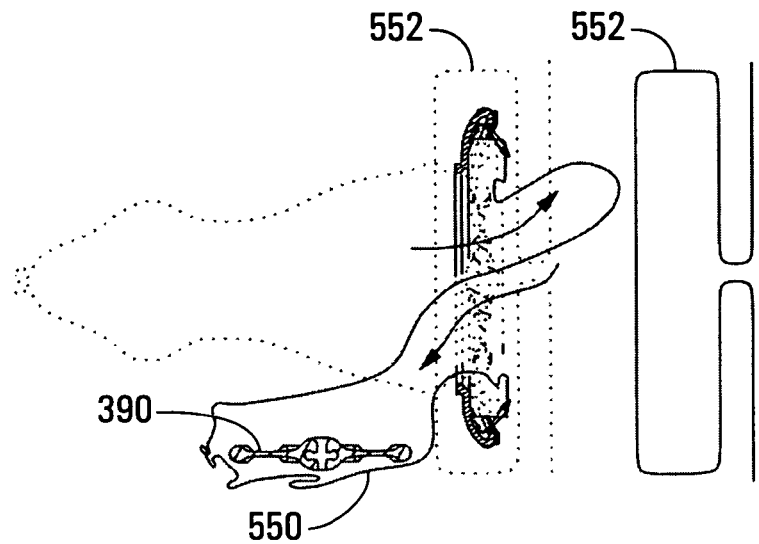
FIG. 52 is a side elevation view of a condom in use for a female.

For example, FIG. 52 illustrates the use of a condom 550 as a female or oral condom. Condom 550 is initially stored in a packaging sheet 552. Sheet 552 is flexible and is folded to enclose condom 550 and a cap 390. Sheet 552 can be removed during use.

Figure 53:
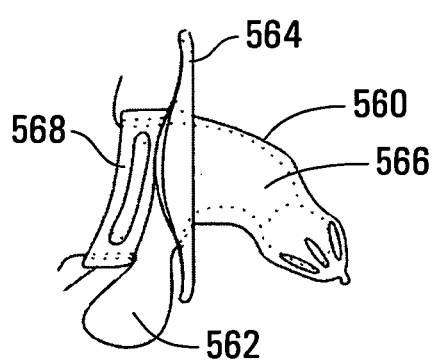
FIG. 53 is a side elevation view of a condom in use for a male.

FIG. 53 illustrates the use of a condom 560 by a male user. Condom 560 is attached to a holder 564, which may include a frame and/or a flange. A placid penis, such as penis 566, may be inserted into condom 560 and may be orally stimulated. As can be seen, the scrotum 562 of the user may be placed behind flange 564. An elastic band/ring 568 is attached to holder 564 and wrapped around scrotum 562. Penis 566 and scrotum 562 may be held or secured in position with an elastic ring, such as ring 568, attached to holder 564. Alternatively, an elastic band may be used to hold the scrotum or around the user's waist with a hook and hoop fastener. Or, a clamp attached to the holder can be used to hold the scrotum between the thighs of either a male or a female user.

Figure 54A:
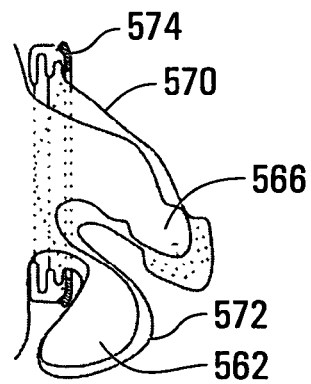
FIG. 54A is a side, partial sectional view of a condom combination in use.
Figure 54B:
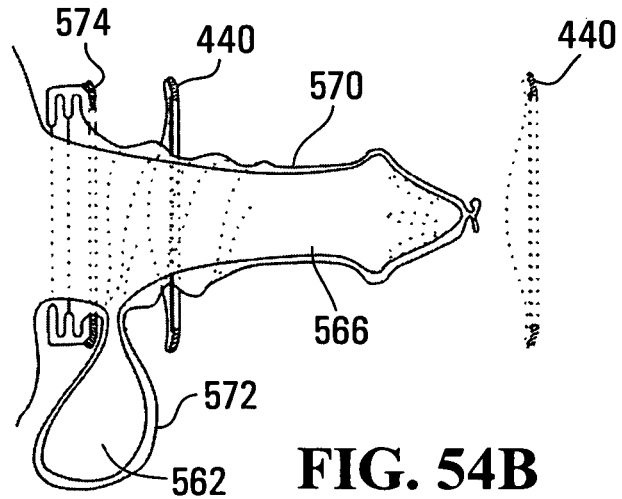
FIG. 54B is a side, partial sectional view of the combination of FIG. 54A in a different position.

FIGS. 54A and 54B illustrate the use of a condom 570 by a male user. As shown in FIG. 54A, a placid penis such as penis 566 may be received in condom 570. Condom 570 has a flexible pocket 572 adjacent the open end of condom 570 for receiving a scrotum, such as scrotum 562. Condom 570 is attached to a frame/flange 574. As can be seen, pocket 572 can be disposed in front of frame/flange 574. Scrotum 562 may be stimulated through pocket 572 and penis 566 may be stimulated, such as orally, through condom 570. As shown in FIG. 54B, when penis 566 becomes erect, condom 570 may be twisted. A front frame 440 may be placed over the twisted condom 570 and erect penis 566. Again, penis 566 and scrotum 562 may be held or secured in condom 570 with an elastic ring or band.

A condom described herein may also be used in combination with other or additional devices or components.

For example, FIGS. 55A and 55B show a massager 580 for use with a loose-fitting condom. Massager 580 has a support frame 582 which supports a flap 584 rotate able about an axle 586. Flap 584 may have a width of about 1 inch and a length of about 0.75 inches. A motor 588 is mounted on frame 582 for rotating axle 586 and thus flap 584, such as at a rotation speed from about 100 to 200 rpm. The speed may be variable. A battery 590 is also mounted on frame 582 for providing power to motor 588. Motor 588 can be turned on or off using a switch 592. A lubricant dispenser 594 is mounted adjacent flap 584 for supplying a lubricant to flap 584 through dispensing holes 596. A ring-shaped attachment 598 is attached to frame 582 for holding massager 580, such as with a finger or a penis. A hook 600 is provided for attaching massager 580 to a frame or support. More hooks may be provided.

Massager 580 can be readily constructed by persons skilled in the art using known techniques.

Massager 580 may be used for automatic massaging or stimulating a body part of a user, such as in combination with another device disclosed herein, during foreplay or intercourse.

Massager 580 can be used for stimulating the female user without excessive stimulation of the male user, thus preventing premature ejaculation, which can be caused by the use of a conventional vibrator.

For example, FIGS. 56A to 56C illustrate a combination of massager 580 and a condom holder 602. Holder 602 has a central opening 604 for receiving a penis or a prosthesis covered with a condom (not shown). Holder 602 may be constructed similarly to a holder described earlier. Massager 580 may be attached to holder 602 with hook 600.

During use, massager 580 may be positioned either above central opening 604 as illustrated in FIG. 56B or below central opening 604 as illustrated in FIG. 56C.

As can be appreciated, the massager can be constructed differently than as shown in FIGS. 55A and 55B. For example, ring-shaped attachment 598 may be replaced with a generally C-shaped attachment 606 as shown in FIG. 57. More than one flap 584 may be operatively connected to motor 588 for automatic massaging of a user during use.

Massager 580 can also be held with a thumb during foreplay and it may have a handle. A protective, flexible sheet may be provided to form a sleeve around massager 580, to protect the user's genital and skin during use.

Figure 58A:
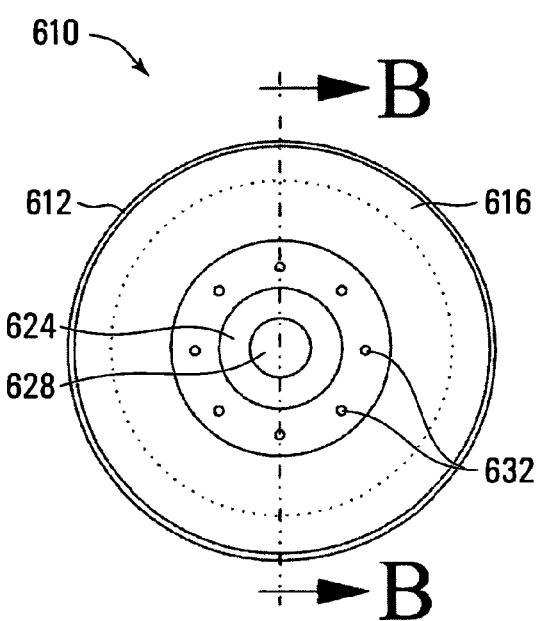
FIG. 58A is a front elevation view of a fluid delivery tube.
Figure 58B:
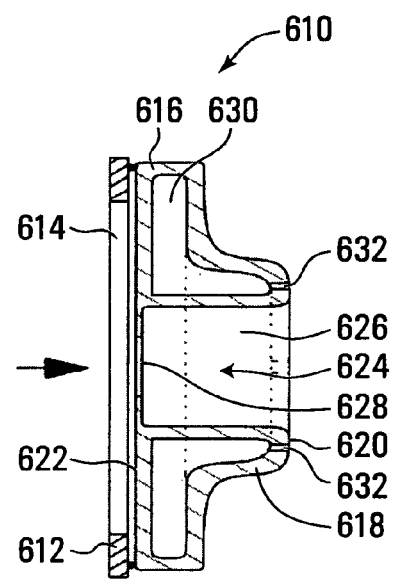
FIG. 58B is a side cross-sectional view of the tube of FIG. 58A along the line B.

FIGS. 58A and 58B illustrate a lubricant delivery tube 610. Tube 610 has a back support 612 with a central opening 614. A fluid storage member 616 is mounted on back support 612. Storage member 616 has a generally tubular and resilient wall 618 extending between opposite sides 620 and 622. Wall 618 defines a channel 624 extending from side 620 to side 622 for receiving a penis or prosthesis covered with a condom. Channel 624 has a wide portion 626 and a narrow portion 628. Wall 618 also defines a fluid chamber 630 for storing and delivering a lubricant (not shown) through a conduit 632. Conduit 632 is sized so that a lubricant can be stored in chamber 630 when wall 618 is under no pressure but can be released from chamber 630 when a sufficient force is applied to wall 618.

Tube 610 can be readily constructed by persons skilled in the art using known techniques.

Figure 59A:
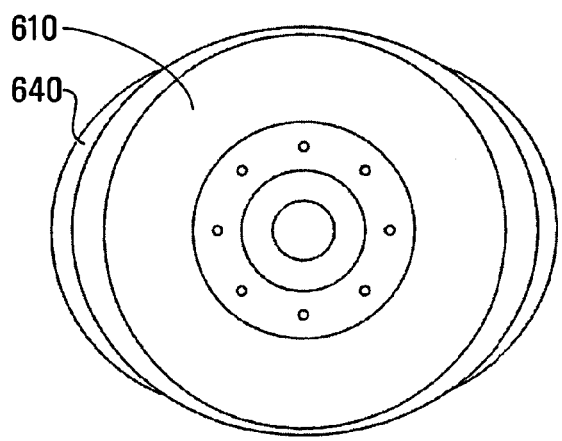
FIG. 59A is a front elevation view of a combination of the tube of FIG. 58A and a holder.
Figure 59B:
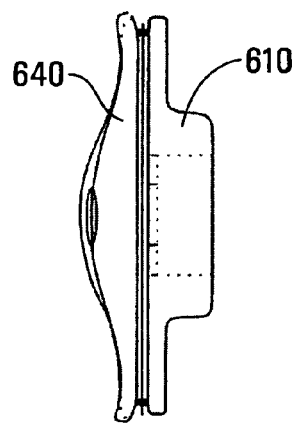
FIG. 59B is a side elevation view of combination of FIG. 59A.

Tube 610 can be attached to a condom holder, such as holder 640, as shown in FIGS. 59A and 59B.

The possible use and variations of tube 610 can be understood by persons skilled in the art after reviewing this paper. For example, when tube 610 is disposed and pressed between two users during use, it can release lubricant periodically and in sync with the users' body motion. A user can also deliberately press tube 610 to release a desired amount of lubricant. Tube 610 may also be held in a users hand, such as on a thumb, during use.

Figure 60:
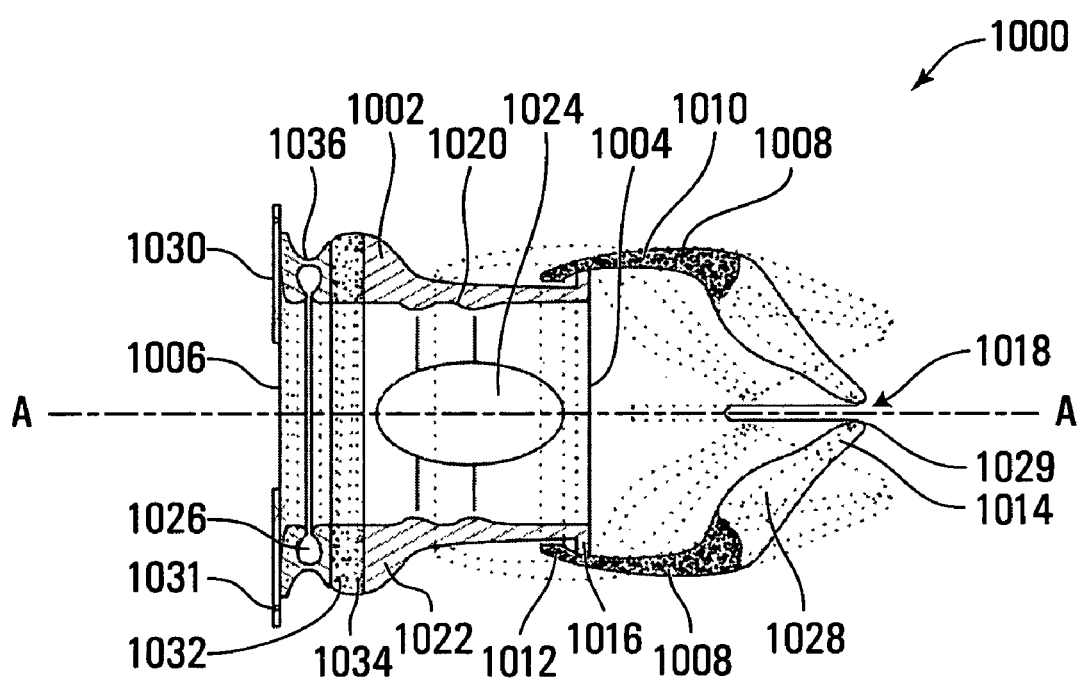
FIG. 60 is a side cross-sectional view of a prosthesis.

FIG. 60 illustrates an external penile prosthesis 1000, exemplary of an embodiment of the present invention. Prosthesis 1000 has a generally tubular body portion 1002 extending about a central axis A. Body portion 1002 has opposite front and rear open ends 1004 and 1006 for receiving the shaft of a penis (not shown) therein.

A head portion 1008 is attached to front end 1004 for covering the glans of the penis received in the body portion. Head portion 1008 can be shaped so that it confirms generally to the shape of the glans. Head portion 1008 can extend along and rotate about axis A. Head portion 1008 includes a number of flaps 1010. Each flap 1010 has a proximal end 1012 which is swing ably attached to body portion 1002. Each flap also has a distal end 1014. Each flap 1010 can swing about an edge 1016 of front end 1004 of body portion 1002, between an open position (as shown in ghost lines) and a closed position (as shown in solid lines). Flaps 1010 define a distal opening 1018 when they are in the open position. Opening 1018 is at least partially closed when flaps 1010 are in the closed position. Opening 1018 can also be adjustable for accommodating a varying size of the penis. In some embodiments, the distal end of head portion 1008 may be closed. If the distal end is closed, a liquid collector may be provided at the closed distal end for collecting and trapping a body fluid released from a user. Head portion 1008 may also be slide ably movable along axis A, as indicated in ghost lines, for adjusting the total length of prosthesis 1000. Edge 1016 of body portion 1002 can serve as a stopper for stopping head portion 1008 from sliding off body portion 1002.

The inner walls 1020 of body portion 1002 may have varying diameters. The exterior walls 1022 of body portion 1002 may also have varying diameters.

Body portion 1002 has one or more side openings or windows 1024 for contacting a penis received therein or for releasing air. Window 1024 can be expandable.

An inner wall of body portion 1002 also defines a circumferentially extending groove 1026 for collecting and storing a body fluid released from a user, or for being used as a fluid reservoir for storing a fluid such as a lubricant. Groove 1026 can also be used for both purposes. For example, a lubricant can be initially stored prior to use, which is released from groove 1026 during use. Subsequently, groove 1026 can receive and store a body fluid discharged by a user.

Head portion 1008 may have a fluid reservoir 1028 (shown in ghost lines) for storing a fluid (not shown), such as a lubricant. The fluid may be released through an opening section 1029 during use onto the penis received within prosthesis 1000. Opening section 1029 may have one or more openings and include a plug made of a spongy material for controlled release of the fluid. Release of the fluid can result when a user applies pressure to head portion 1008. As can be appreciated, the thrusting motion of the user during use can apply a varying pressure to head portion 1008 and cause repeated release of the fluid. As shown, reservoir 1028 is formed in the wall of head portion 1008. However, as can be understood, a fluid reservoir for lubricant can also be formed in body portion 1002, or elsewhere but is connectable to either body portion 1002 or head portion 1008.

Prosthesis 1000 may include a flange-like end member 1030 attached to rear end 1006. Holes 1031 are provided for attaching end member 1030 and thus prosthesis 1000 to a condom holder or frame, such as one of those described above, with a fastener (not shown). End member 1030 can also serve as a protective guard when the prosthesis is used as a plug.

Body portion 1002 can be axially extendable and retractable. Body portion 1002 can also be radially expandable. In this regard, body portion 1002 may be made of a flexible or elastic material. For example, body portion 1002 may have a section 1032 that is more flexible than other sections. Section 1032 may be made of a springy or non-springy, soft material for pliability, extendibility, and shock absorption. Section 1032 may include a foam material and an enclosure enclosing a spring 1034. Spring 1034 can be used to axially extending or retracting body portion 1002. Spring 1034 can be a coil spring. In a different embodiment, the coiled spring may be replaced with a coiled wire, which is extendable and compressible but not resilient.

Further, body portion 1002 may have a weakened section 1036 which will facilitate folding or flattening of prosthesis 1000.

In a different embodiment, prosthesis 1000 may include an actuator for axially extending and retracting body portion 1002. The actuator may be manually operable or drivable by an electrical motor.

Body portion 1002 and head portion 1008 can both be deformable such that they can be flattened laterally, relative to the central axis.

Body portion 1002 and head portion 1008 can be made of any suitable material. Each of them can be made of a flexible material, a semi-rigid material, or a rigid material. For example, a suitable material can be selected from paper, fabric, plastic, and rubber. The material can be firm or soft but firm enough for insertion during intercourse, as can be understood by persons skilled in the art.

As can be appreciated, in different embodiments, head portion 1008 can have different structures, shape and sizes. For example, head portion 1008 may have one or more flaps. Flaps may be merely rotate able but not swing able, or swing able but not rotate able.

As can be understood by a person skilled in the art, a vibrator (not shown) may be disposed within head portion 1008. The vibrator may be used to stimulate a user.

A person skilled in the art can readily construct prosthesis 1000 after reviewing this paper.

Prosthesis may be used in combination with other components described herein, such as package 540 as illustrated in FIGS. 61A, 61B, 62A, and 62B.

Figure 61A:
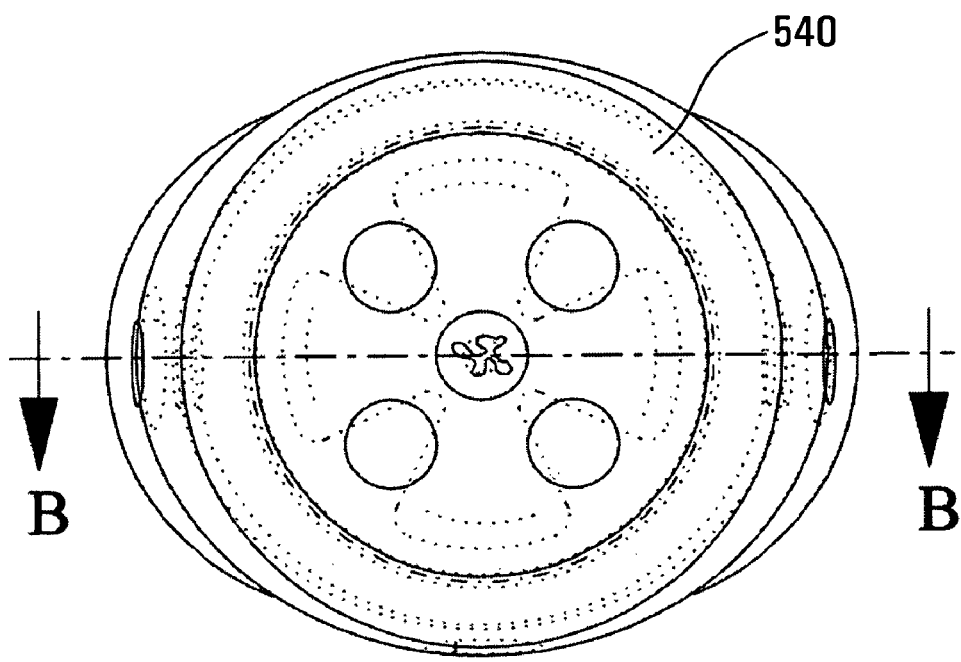
FIG. 61A is a front elevation view of a combination of the package of FIG. 51A and the prosthesis of FIG. 60.
Figure 61B:
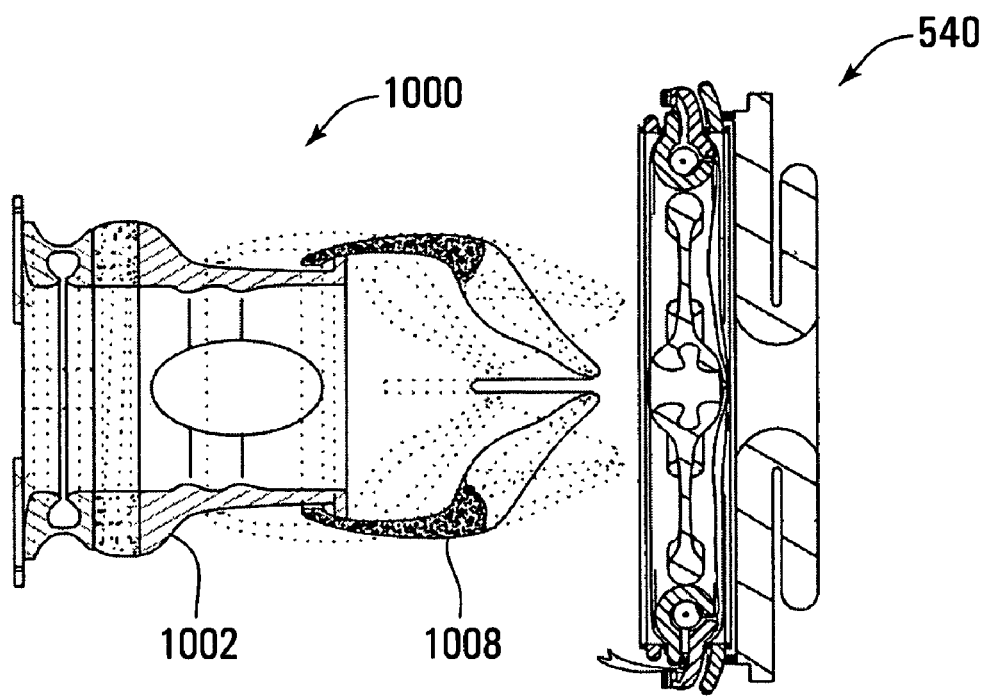
FIG. 61B is a cross-sectional view of the combination of FIG. 61A along the line B.
Figure 62A:
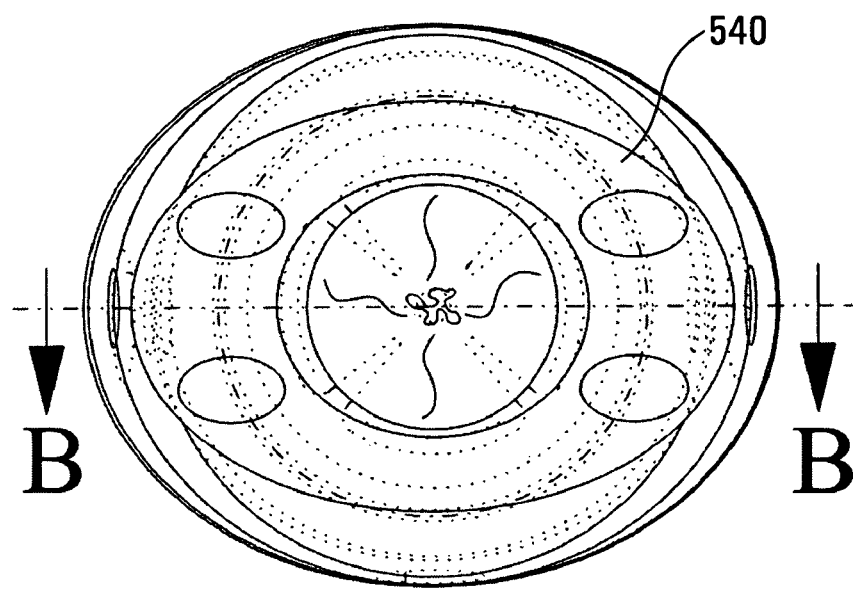
FIG. 62A is a front elevation view of the combination of FIG. 61A in use.
Figure 62B:
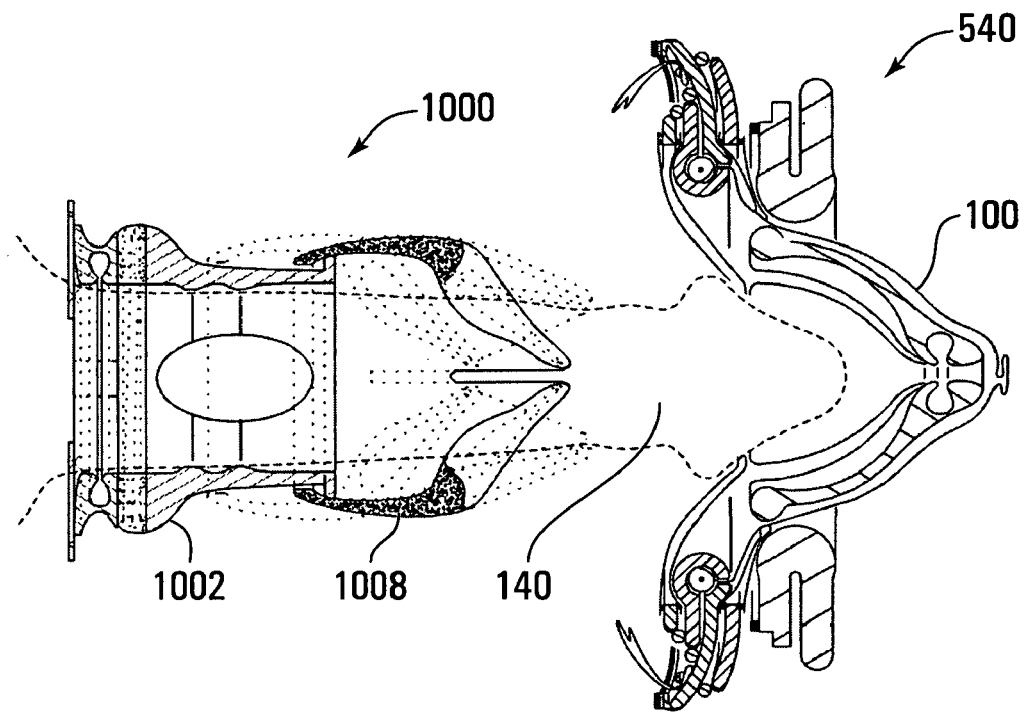
FIG. 62B is a cross-sectional view of the combination of FIG. 62A along the line B.

During use, prosthesis 1000 and package 540 may positioned as better shown in FIGS. 61B and 62B. Condom 100 is initially rolled up, folded or collapsed. A penis 140 is inserted into prosthesis 1000, through body portion 1002 and then head portion 1008, and eventually into and through the central openings in package 540. Prosthesis 1000 may also be inserted through the central openings of package 540. As the penis/prosthesis is inserted, condom 100 is unrolled, unfolded or expanded, and covers the penis/prosthesis.

As described above, condom 100 has a loose-fitting portion which loosely covers a shaft portion of the penis/prosthesis. After the penis/prosthesis is fully inserted, condom 100 may be twisted and secured in the twisted state as described before. For this purpose, an end of condom 100 may be conveniently rotated by rotating head portion 1008 of prosthesis 1000. Condom 100 may also be secured by securing package 540 in position.

As can be appreciated, prosthesis 1000 can also be used with a tight-fitting condom and without twisting.

Figure 63:
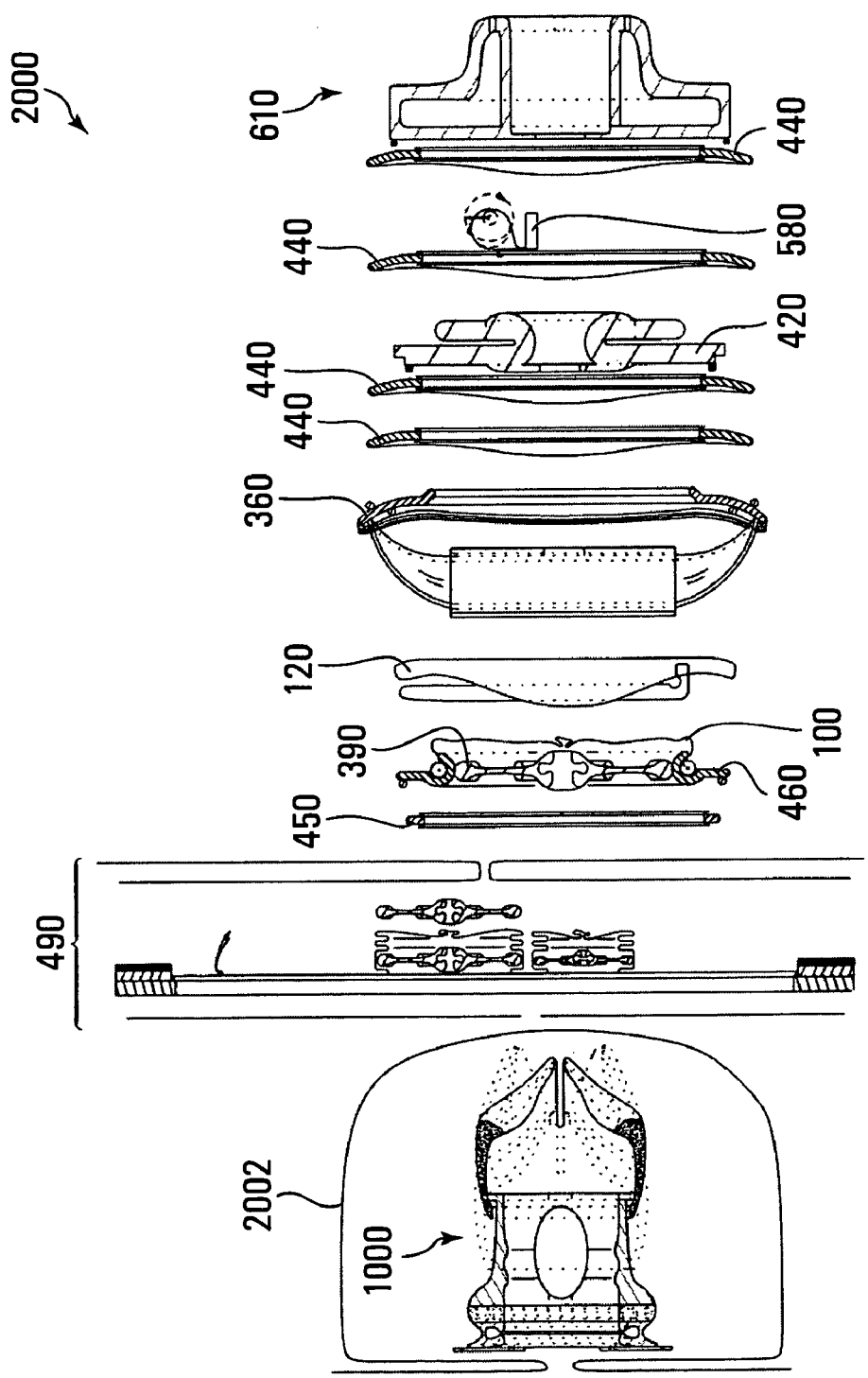
FIG. 63 is an exploded cross-sectional view of a combination including the condom of FIG. 1A and prosthesis of FIG. 60.

FIG. 63 illustrates a combination 2000, showing the relative positions of various components described herein during use. Combination 2000 includes prosthesis 1000 enclosed in a protective sheet 2002 which can be similar to sheet 552, package 490, frame 450, housing member 460, flap 390, condom 100, holder 120, holder 360, frames 440, constriction ring 420, massager 580, and tube 610.

During use, a penis (not shown) may be inserted through each component in combination 2000, except the condoms, as can be appreciated and understood by persons skilled in the art.

In different applications, more or fewer components may be used. Each component may also be substituted as can be understood by persons skilled in the art.

FIGS. 64A to 64C illustrate another prosthesis 1050 and its use. Prosthesis 1050 is similar to prosthesis 1000. It has a tubular body 1052 and a rotate able head 1054. Head 1054 has a proximal end 1056 and a distal end 1058. Body 1052 has a front end 1060 and a rear end 1062. The rear end 1062 of body 1052 can be covered with a protective sheet such as sheet 472 as shown. Proximal end 1056 of head 1054 is received in a groove 1064 formed on body 1052 at front end 1060. Distal end 1058 defines a central opening 1066 sized for receiving an erect penis (not shown). A side window 1068 is provided on body 1052 for contacting the penis received therein, or for releasing air there from.

As shown, prosthesis 1050 is covered by a first, inside condom 1070, and a second, outside condom 1072, both of which are attached to housing member 460 and holder 360. Prosthesis 1050, with the covering condoms, may be inserted through a front frame 440.

As in prosthesis 1000, body 1052 of prosthesis 1050 may have one or more flexible sections. For example, it may have a firm base 1074 and softer and longitudinally extending sections 1076. Softer sections 1076 can facilitate folding or flattening of prosthesis 1050. Prosthesis 1050 can be made of a material selected from pliable, elastic, flexible, bendable, soft, and biodegradable materials. Thus, prosthesis 1050 can be flattened as shown in FIG. 65.

A person skilled in the art can readily understand and make prosthesis 1050 after reviewing this paper.

In use, a penis may be received in prosthesis 1050. Rotate able head 1054 may be rotated to twist condoms 1070 and 1072. Prosthesis 1050 can be used in a manner similar to that for prosthesis 1000.

FIG. 66 shows another prosthesis 1100, which is similar to prosthesis 1050, except that prosthesis 1100 includes a rotate able head 1102 which has a smaller distal opening 1104 for allowing air to pass there through.

FIGS. 67A to 67D show a further prosthesis 1110. Prosthesis 1110 is similar to prosthesis 1000 and can be used similarly. However, prosthesis 1110 has a base 1112 and four protective guards 1114 at its rear end. One end of each guard 1114 is attached to base 1112 and the other end can be attached to a holder such as holder 360. Guards 1114 are distributed circumferentially. Guards 1114 can be plate-like shaped and can be thin. Guards 1114 are hingedly mounted and can swing about relative to base 1112. Thus, prosthesis 1110 can be flattened, as shown in FIG. 67C, by a user with ease, even when guards 1114 are made of a rigid and strong material.

As illustrated in FIGS. 67B and 67D, holder 360 can be attached either to base 1112 or guards 1114.

FIG. 68 shows the use of prosthesis 1000 which is positioned between condoms 1070 and 1072. As can be appreciated, in this arrangement, condom 1070 can be used to separate prosthesis 1000 from the penis to be received therein.

Figure 69:
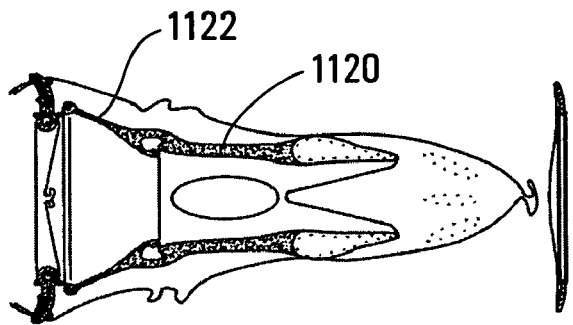
FIGS. 69, 70A, 70B, 71, 72A, and 72B are side cross-sectional views of respective combinations including respective prostheses.

FIG. 69 illustrates another prosthesis 1120. Prosthesis 1120 is formed of a single piece and has a thin-wall portion 1122 for increased flexibility, pliability and shock absorption.

Figure 70A:
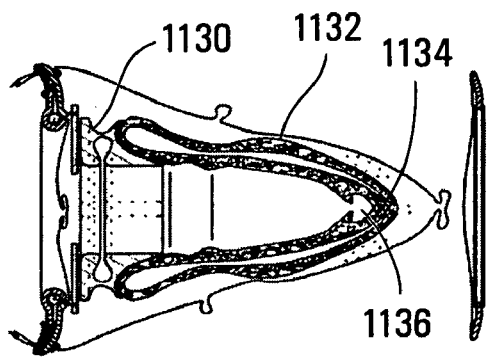
Figure 70B:
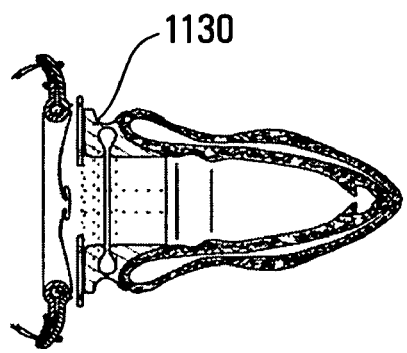

FIGS. 70A and 70B show a prosthesis 1130, which is similar to prosthesis 1110. However, prosthesis 1130 includes a head 1132 which has a closed distal end 1134. A chamber 1136 is formed at distal end 1134 for receiving and trapping ejaculated body fluid. Prosthesis 1130 can be used in either of the arrangements shown in FIGS. 70A and 70B.

Figure 71:
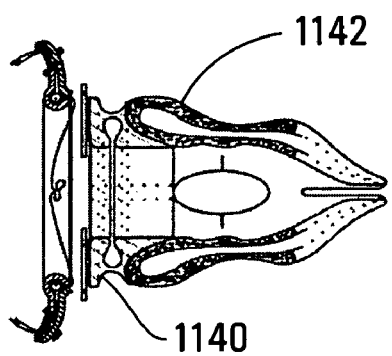

FIG. 71 shows a prosthesis 1140, which is similar to prosthesis 1130 but with a different head 1142, as can be seen and understood by comparing FIGS. 70B and 71.

Figure 72A:
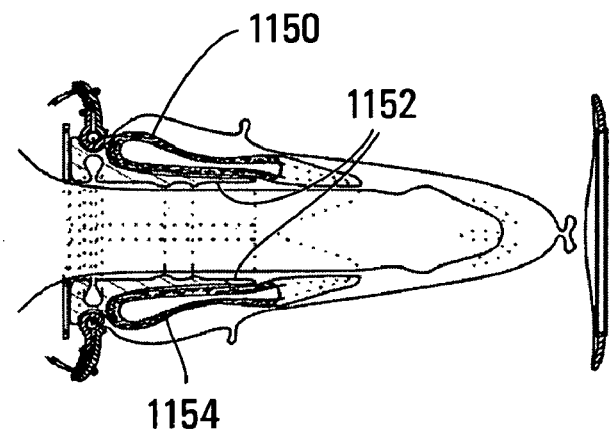
Figure 72B:
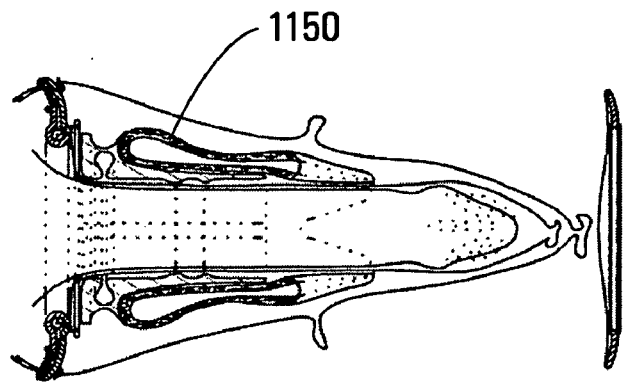

FIGS. 72A and 72B show a prosthesis 1150 in different use arrangements. Prosthesis 1150 is similar to prosthesis 1140 but has an extended body 1152 which provides improved support for head 1154.

FIGS. 73A to 73D show a prosthesis 1160, which is similar to prosthesis 1000. However, the rear guards 1162 of prosthesis 1160 extend radially farther beyond body portion 1164, as compared to that of prosthesis 1000. On the front side of guard 1162, projections 1166 are formed for stimulating a female user. Prosthesis 1160 is flexible and deformable so that it can be flattened for storage, as shown in FIGS. 73C and 73D.

FIG. 74 shows two prostheses 1170 attached to a condom holder 360. This combination may be used by two female users, as will be understood by persons skilled in the art.

Figure 75C:
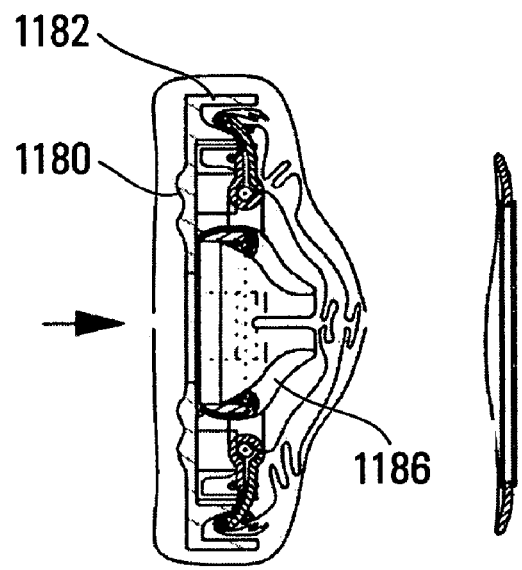
FIG. 75C is a side cross-sectional view of a package including the prosthesis of FIG. 75A in a retracted position for storage.
Figure 75D:
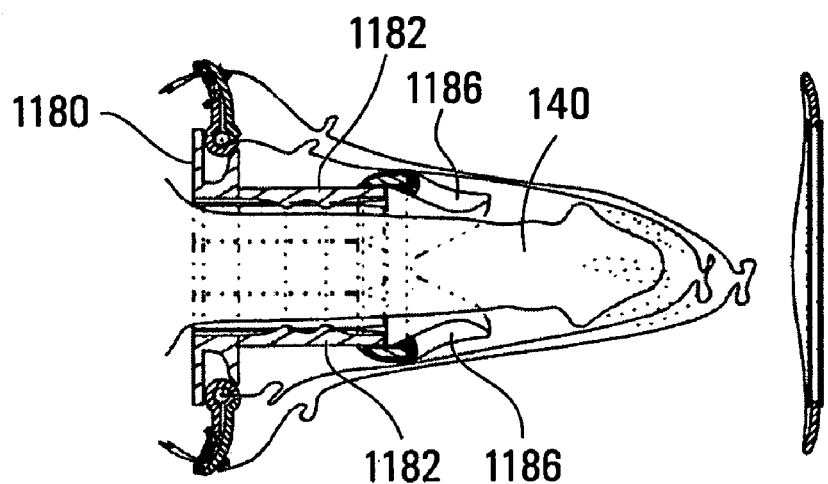
FIG. 75D is a side cross-sectional view of the package of FIG. 75C in an extended position during use.

FIGS. 75A and 75B show a prosthesis 1180 having longitudinal segments 1182. Each segment 1182 is hinged, at hinge 1184, to a head 1186. Segments 1182 can swing about hinges 1184 between a flat position and a tube position. In the flat position, segments 1182 extend radially outward, as shown. Segments 1182 may be in the flat position when prosthesis 1180 is not in use, as shown in FIG. 75C. During use, segments 1182 may be rotated to the tube position and extend axially as shown in FIG. 75D, thus forming a tube-shaped body for receiving a penis 140 there in between. Prosthesis 1180 can be packaged and used together with other components described herein, such as illustrated in FIGS. 75C and 75D. As illustrated, segments 1182 can have suitable corresponding shapes for use and storage with the other components.

FIG. 76A to 76C show a prosthesis 1190 in a package 1192. An adhesive material may be applied to the rear end 1194 of prosthesis 1190. Prosthesis 1190 is enclosed in a protective sheet 1196. In use, protective sheet 1196 can be opened to expose the adhesive rear end 1194 which can then be attached to a user, or a holder. Prosthesis 1190 has a number of telescopic tubes 1198, which form the body of prosthesis 1190. For example, it can have three telescopic tubes as shown.

As can be understood, prosthesis 1190 can move between a compacted or retracted position, as shown in FIG. 76B, and an extended position, as shown in FIG. 76C. The extended length of prosthesis 1190 can thus be easily adjusted to suit different users or for different situations.

Tubes 1198 may have different sizes for smooth sliding movement. Stoppers or locking mechanisms (not shown) may be provided thereon for preventing separation of the tubes and for locking the tubes in position. Such stoppers and locking mechanisms may include pins, holes, rubber rings and ridges formed on the walls of the tubes. The construction and use of telescopic tubes can be readily understood by persons skilled in the art.

In different embodiments, the inner and outer walls of the telescopic tubes may also have corresponding and engaging spiral ridges (not shown) so that relative rotation of the tubes can cause extension or reduction of the overall length. Thus, extension of the prosthesis and twisting of the condom covering the prosthesis can be achieved with a single rotation motion.

As can be understood, prosthesis 1190 may be modified to include an elastic coil (not shown) for actuating the telescopic tubes. The coil may be placed either inside or outside the tubes. The two ends of the coil may be attached to the two opposite ends of the tubes respectively. The coil may be a compression coil which has sufficient resistance to withstand pressure applied during insertion or handling of the prosthesis. The coil may be covered with a suitable material such as a soft material. Generally, the outer surface of the coil should feel stimulating, soft and comfortable.

In different embodiments, the coil can be springy or non-springy. A non-springy coil can be useful for quickly adjusting the length of the prosthesis. The coil may also have both a springy portion and a non-springy portion.

As can be appreciated, when a penis received in the prosthesis loses its erection and retracts into the prosthesis during intercourse, the prosthesis can maintain its length and can be used to continue stimulation of the female user. In addition, if a cap 390 is used, cap 390 may be stopped at the front end of the prosthesis, which can also be used to stimulate the female user.

Figure 77A:
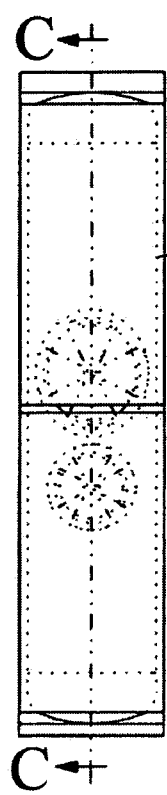
FIGS. 77A and 77B are respectively front and rear elevation views of a combination including the package of FIG. 42A and prosthesis in FIG. 76B.
Figure 77B:
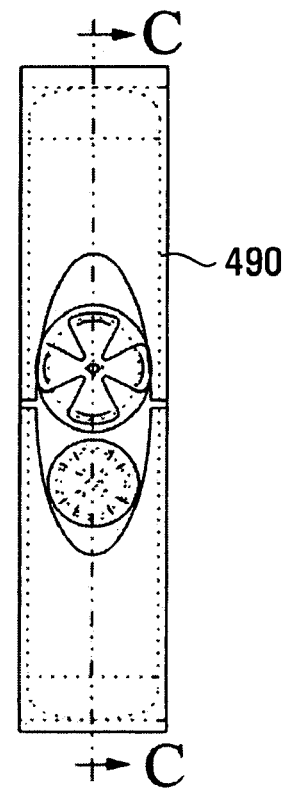
Figure 77C:
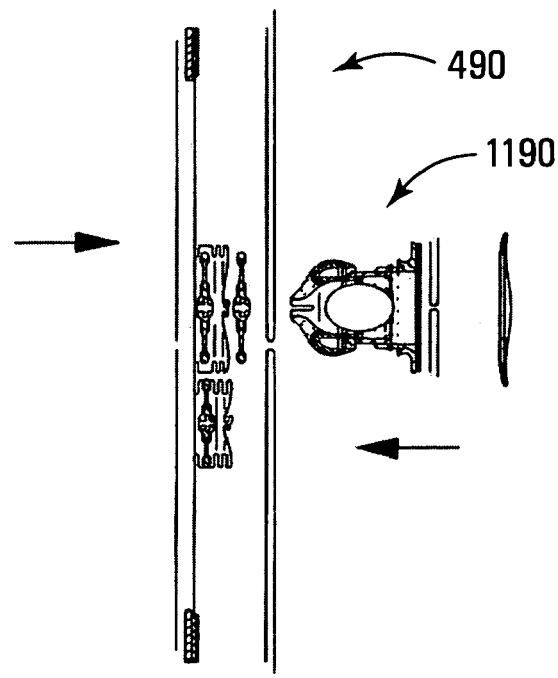
FIG. 77C is a cross-sectional view of the combination of FIGS. 77A and 77B along the line C.

FIGS. 77A to 77C illustrate the use of prosthesis 1190 and package 490 in combination, which can be readily understood by a person skilled in the art.

Figure 78A:
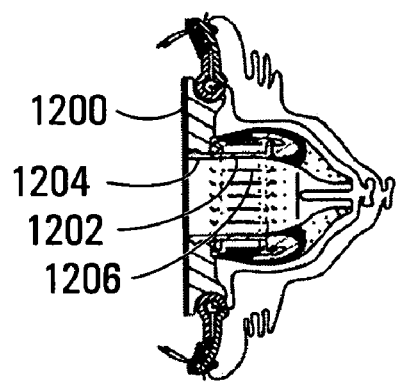
FIGS. 78A and 78B are side cross-sectional views of a combination including an extendable prosthesis respectively in retracted and extended positions.
Figure 78B:
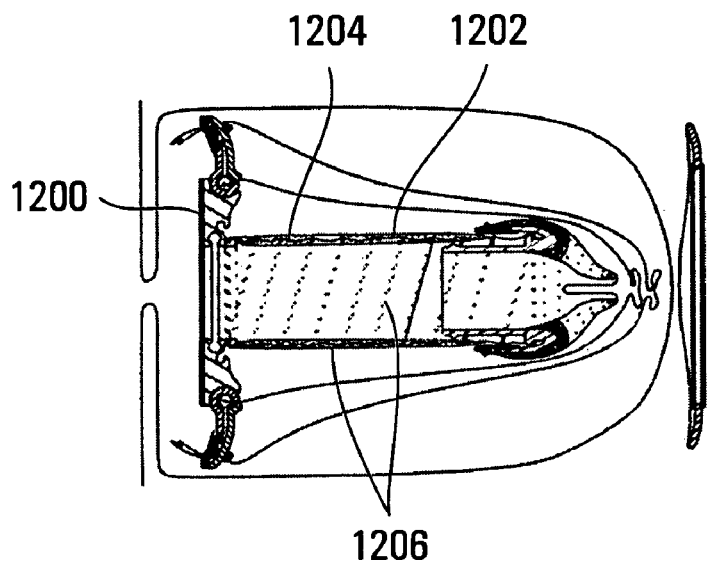

FIGS. 78A and 78B show a prosthesis 1200, which has an enclosure 1202 in its body 1204. A cylindrical coil 1206 is enclosed in enclosure 1202. Coil 1206 is resilient. The body material is elastic. Coil 1206 abuts body 1204 and urges it to extend. Thus, body 1204 can extend or retract depending on whether an external pressure is applied to counter the abutting force of coil 1206, as illustrated.

Figure 79:
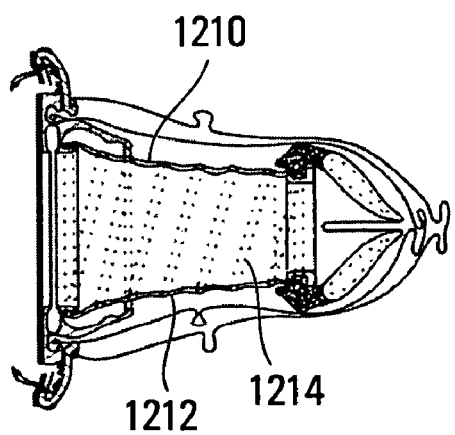
FIG. 79 is a side cross-sectional view of a combination including another extendable prosthesis.

FIG. 79 shows a prosthesis 1210 similar to prosthesis 1200, except that the coiled portion 1212 and the coil 1214 in prosthesis 1210 are generally cone-shaped. An advantage of a cone-shaped body is that the body can easily collapse into a flat form. Coil 1214 in coil portion 1212 can be covered with an elastic, flexible, soft, and pliable material, which can be biodegradable.

As can be understood, instead of using a spring to actuate extension of the body of a prosthesis, an expandable chamber in the prosthesis body can be connected to a container so that they are in fluid communication. In use, the container can be filled with a compressed fluid, such as a lubricant, air, water, or the like. The compressed fluid can be released from the container and fed into the expandable chamber for axially extending or radially expanding the body of the prosthesis.

Other actuating mechanisms, such as mechanical or electrical actuating mechanisms may also be used for extending or shortening the prosthesis. Such mechanisms may include an electronic circuit, battery, motor, gear, switch and the like. Such mechanisms can be readily understood by persons skilled in the art.

The head portion of a prosthesis may also include a built-in vibrator for stimulating a user, such as a female user.

As now can be appreciated, the exemplary condoms described above can be conveniently used to cover a penis, a prosthesis or a penis-like figure such as a finger, or to be inserted into a female's vagina. For holding or securing a condom in place, the condom may be attached to any suitable holder such as one of the exemplary holders, frames, prostheses, and other components described above. The condom can be twisted by twisting one or more of the components to which it is attached.

As can be understood, some of the components described above can be interchangeable. For example, a holder can be a frame, a collar, a ring, a flange, or a prosthesis, or vice versa. Similarly, many of the components described can be made of a material that is pliable, elastic, flexible, bendable, soft, rigid, or semi-rigid. The material can also be biodegradable. The material can be selected from paper, fabric, plastic, rubber, and the like.

When desired, other devices may also be used or attached to an exemplary embodiment described above. For example, micro sound devices and flicking lights may be added, for fun and entertainment.

As can be appreciated, embodiments of the present invention provide users with methods and tools for improving their enjoyment of sexual activities. Users can choose from a variety of alternatives based on their personal preferences.

The embodiments of the present invention can be versatile, joyful, attractive, sexually appealing, desirable, handy, easy and convenient to use, practical, compact, hygienic, and maintenance free. They can be fun and entertaining to use and can feel natural. They can be used by users of different background, sex, age, and sexual orientation. They can be used in a variety of sexual activities, including intercourse and oral sex, and meet different demands of different users. As a result, more users will likely use condoms more often.

The embodiments of this invention can be used to encourage sexually active people to practice fulfilling, healthy and safe sex. They can also be used for birth control, and for treatment of different ailments and disabilities.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. An external penile prosthesis, comprising:
a generally tubular body portion extending about a central axis and having opposite first and second open ends for receiving a penis therein; and
a head portion attached to said first end of said body portion for covering the glans of said penis, said head portion extending along said central axis and rotatable thereabout, said head portion comprising a plurality of flaps, each one of said flaps having a proximal end swingably attached to said body portion and a distal free end, said flaps swingable about an edge of said first end of said body portion between a closed position and an open position, wherein in said open position said free ends of said flaps define an opening and in said closed position said opening is at least partially closed.

2. The prosthesis of claim 1, wherein said body portion is axially extendable and retractable.

3. The prosthesis of claim 2, wherein said body portion comprises a plurality of telescopic tubes.

4. The prosthesis of claim 2, wherein said body portion comprises an elastic material.

5. The prosthesis of claim 2, wherein said body portion comprises a deformable material.

6. The prosthesis of claim 5, wherein said body portion comprises a spring for axially extending or retracting said body portion.

7. The prosthesis of claim 6, wherein said body portion further comprises an enclosure enclosing said spring.

8. The prosthesis of claim 6, wherein said spring is a coiled spring.

9. The prosthesis of claim 2, wherein said body portion comprises an enclosure and a non-resilient coiled wire enclosed therein, said coiled wire being extendable and compressible.

10. The prosthesis of claim 2, wherein said body portion and said head portion are deformable such that said body portion and said head portion can be flattened laterally.

11. The prosthesis of claim 2, wherein said body portion is radially expandable.

12. The prosthesis of claim 1, wherein said body portion has varying inner diameters.

13. The prosthesis of claim 1, wherein at least one of said body portion and said head portion comprises a material selected from paper, fabric, plastic, and rubber.

14. The prosthesis of claim 1, wherein at least one of said body portion and said head portion is made of a flexible material.

15. The prosthesis of claim 1, wherein at least one of said body portion and said head portion is made of a semi-rigid material.

16. The prosthesis of claim 1, wherein at least one of said body portion and said head portion is made of a rigid material.

17. The prosthesis of claim 1, wherein said head portion is shaped to confirm generally to the shape of said glans of said penis.

18. The prosthesis of claim 2, further comprising an actuator drivable by an electrical motor for axially extending and retracting said body portion.

19. The prosthesis of claim 2, further comprising a manual actuator operable by a human for axially extending and retracting said body portion.

20. The prosthesis of claim 2, wherein said body portion defines an expandable chamber, said prosthesis further comprising a container containing a compressed fluid, said container connectable to said expandable chamber to be in fluid communication therewith such that said compressed fluid is releasable from said container into said expandable chamber for axially extending or radially expanding said body portion, or axially extending and radially expanding said body portion.

21. The prosthesis of claim 20, wherein said fluid is selected from air and water.

22. The prosthesis of claim 1, further comprising an attachment member attached to said second end of said body portion, for attaching said prosthesis to a condom.

23. The prosthesis of claim 1, further comprising a fastener attached to said second end of said body portion, for securing said prosthesis over said penis.

24. The prosthesis of claim 1, wherein each one of at least one of said body portion and said head portion has at least one opening for contacting said penis received therein or for releasing trapped air.

25. The prosthesis of claim 24, wherein said at least one opening is expandable.

26. The prosthesis of claim 1, further comprising a reservoir containing a liquid, said reservoir connectable to one of said body portion and said head portion such that said liquid is releasable from said reservoir onto said penis received in said prosthesis.

27. The prosthesis of claim 26, wherein said liquid is a lubricant.

28. The prosthesis of claim 26, wherein said reservoir is contained within a wall of said head portion or said body portion.

29. The prosthesis of claim 1, wherein said head portion has an open distal end, said distal end having an opening to allow said penis to pass through.

30. The prosthesis of claim 29, wherein said opening of said distal end of said head portion is adjustable for accommodating a varying size of said penis.

31. The prosthesis of claim 1, further comprising a vibrator disposed within said head portion.

32. The prosthesis of claim 1, wherein said body portion has varying external diameters.

33. The prosthesis of claim 1, wherein said body portion has a groove circumferentially extending on an inner wall of said body portion for collecting a body fluid released from a user or storing a lubricant, or for storing a lubricant and collecting a body fluid released from said user.

34. A combination comprising the prosthesis of claim 1 and a loose-fitting condom comprising a flexible sheath, said sheath having a closed end and an open end, said open end of said sheath defining an opening for reception of a shaft having a central axis, said shaft being one of a penis and said prosthesis, said sheath having a loose-fitting portion sized for loosely covering said shaft.

35. The combination of claim 34, wherein said sheath has a neck portion between said loose-fitting portion and said closed end, said neck portion being elastic and sized for close-fit over and frictional engagement with a head portion of said shaft to allow said sheath being twisted by rotating said closed end of said sheath.

36. The combination of claim 34, further comprising a holder for holding said loose-fitting condom in a twisted position in which said sheath is twisted such that said loose-fitting portion of said sheath closely covers said shaft, said holder having an aperture sized for reception and engagement with said sheath over said shaft.

37. The combination of claim 36, wherein said holder is elastic.

38. The combination of claim 36, wherein said holder is rigid or semi-rigid.

39. The combination of claim 36, wherein said holder is absorbent.

40. The combination of claim 36, wherein said holder is spongy.

41. The combination of claim 36, wherein said holder comprises a holding and handling member attached to said sheath adjacent said open end of said sheath, said holding and handling member attachable to a user for securing said sheath over said shaft.

42. The combination of claim 41, wherein said holding and handling member comprises a plurality of separated segments attached to said sheath adjacent the periphery of said opening at said open end of said sheath.

43. The combination of claim 41, wherein said holding and handling member comprises a flange, said flange having an aperture for receiving said shaft covered by said sheath.

44. The combination of claim 43, wherein said aperture of said flange has a diameter of about 1.5 inches to about 15 inches.

45. The combination of claim 43, wherein said aperture of said flange has a diameter larger than a diameter of said shaft.

46. The combination of claim 43, further comprising a soft absorbent sealing pad attached to said flange adjacent an outer periphery of said flange.

47. The combination of claim 43, wherein said flange has a radially outward-facing surface adjacent an outer periphery of said flange, said surface being slip resistant so as to facilitate handling of said loose-fitting condom.

48. The combination of claim 43, wherein said flange has a generally hemispherical shape.

49. The combination of claim 43, wherein said flange has a generally disk-like shape.

50. The combination of claim 41, further comprising a securing member selected from a band, a hook, a clamp, a loop, a ring, and an adhesive tape, said securing member attached to said holding and handling member for securing said sheath over said shaft.

51. The combination of claim 50, further comprising a fastener for attaching said securing member to said holding and handling member.

52. The combination of claim 50, wherein said band is attached to a pad to be placed behind the scrotum of a user so as to secure said loose-fitting condom over said shaft.

53. The combination of claim 43, wherein said flange has a contoured surface such that said contoured surface is in substantial conformity with a surface of a user's body with which said flange is in contact during use.

54. The combination of claim 41, wherein said holding and handling member has an adhesive surface for attachment to said user.

55. The combination of claim 41, wherein said holding and handling member is formed of a semi-rigid or rigid material.

56. The combination of claim 34, wherein a portion of said sheath adjacent said open end of said sheath fits closely over a base portion of said shaft.

57. The combination of claim 56, wherein said portion adjacent said open end of said sheath is elastic and said opening is sized such that said open end of said sheath is in sealing and frictional engagement with said base portion of said shaft during use.

58. The combination of claim 34, wherein said opening at said open end of said sheath is large enough to receive the scrotum of a user, and said sheath further defines a pocket near said open end of said sheath for receiving and retaining said scrotum therein when said shaft is received.

59. The combination of claim 34, further comprising an elastic and generally fan-shaped extension member, said extension member receivable in said sheath between said sheath and said shaft for expanding said sheath.

60. The combination of claim 59, wherein said extension member has a plurality of flaps connected to a central web, said flaps naturally radially extending and foldable under pressure.

61. The combination of claim 60, wherein each one of said flaps of said extension member has a thickened tip.

62. The combination of claim 60, wherein said web of said extension member defines a central aperture for air release.

63. The combination of claim 60, wherein said web of said extension member defines a chamber for trapping a body fluid released by a user.

64. The combination of claim 60, wherein each one of said flaps of said extension member defines a through hole for allowing a foreign object to exert a force on said shaft covered by said each flap.

65. The combination of claim 60, wherein said extension member is one of a plurality of extension members, each one of said extension members having a distinct color.

66. The combination of claim 60, wherein said extension member has a radially contoured surface.

67. The combination of claim 35, wherein said neck portion of said sheath is thicker than said loose-fitting portion of said sheath.

68. The combination of claim 34, wherein said closed end of said sheath is tapered and thickened.

69. The combination of claim 34, wherein said closed end of said sheath has at least one projection extending outwardly from an external surface of said closed end.

70. The combination of claim 34, further comprising a flexible shield for shielding at least an end of said sheath.

71. The combination of claim 70, wherein said shield comprises two flexible sheets, each for shielding one of said closed and open ends of said sheath.

72. The combination of claim 34, wherein a portion of said sheath has varying internal diameters.

73. The combination of claim 34, wherein a portion of said sheath has varying external diameters.

74. The combination of claim 43, further comprising a flexible container attached to said flange for collecting and storing a body fluid discharged from a user.

75. The combination of claim 36, wherein said holder comprises a generally ring-shaped collar.

76. The combination of claim 75, wherein said collar is one of a plurality of collars, each one of said collars having a distinct color.

77. The combination of claim 43, further comprising a housing member for housing said sheath.

78. The combination of claim 77, wherein said sheath is stored in said housing member prior to use.

79. The combination of claim 77, wherein said housing member has a generally annular shape defining an aperture for reception of said shaft therethrough and is substantially coaxially attached to said flange.

80. The combination of claim 79, wherein said housing member defines a circular groove adjacent an edge of said aperture of said flange for receiving and confining said open end of said sheath therein.

81. The combination of claim 34, wherein said loose-fitting condom comprises a flared lip connected to and adjacent said open end of said sheath, said flared lip defining an aperture for passage of said shaft and flaring radially outwardly.

82. The combination of claim 81, wherein said flared lip is elastic and its aperture has an initial diameter substantially smaller than a diameter of said shaft.

83. The combination of claim 82, wherein said initial diameter of said aperture of said flared lip is more than about 0.3 inch.

84. The combination of claim 81, wherein said flared lip is thicker than a tubular portion of said sheath adjacent said flared lip.

85. The combination of claim 34, wherein a surface of said loose-fitting condom is treated with at least one of a medicament, a lubricant, and a contraceptive material.

86. The combination of claim 34, wherein said sheath is a first sheath, said loose-fitting condom further comprising a second sheath having a closed end and an open end, said open ends of said first and second sheaths disposed near each other.

87. The combination of claim 86, wherein said closed ends of said first and second sheaths extendable toward opposite directions.

88. The combination of claim 86, wherein said closed ends of said first and second sheaths extendable toward the same direction.

89. The combination of claim 34, wherein said sheath has a tubular wall of a thickness of about 0.01 mm to about 2 mm.

90. The combination of claim 34, wherein said loose-fitting condom comprises a material selected from a prophylactic material, a flexible material, and an elastic material.

91. The combination of claim 34, wherein said loose-fitting condom is initially in a rolled-up, folded, or collapsed state before use.

92. The combination of claim 79, wherein said holder further comprises a ring-shaped frame substantially coaxially attached to a side of said flange.

93. The combination of claim 92, wherein said holder further comprises another ring-shaped frame substantially coaxially attached to another side of said flange.

94. The combination of claim 92, wherein said housing member is substantially coaxially attached to said ring-shaped frame.

95. The combination of claim 92, wherein said ring-shaped frame is sized for frictional engagement with said sheath when said shaft is received in said sheath.

96. The combination of claim 92, further comprising an elastic constriction ring mountable over said sheath when said sheath covers said shaft, said constriction ring defining a central opening for receiving and frictionally engaging said sheath over said shaft, said constriction ring further defining a plurality of peripheral openings to allow insertion of a human finger for stretching said central opening of said constriction ring.

97. The combination of claim 96, wherein said constriction ring has a total thickness of about 5 mm or about 7 mm and comprises two overlaying layers of elastic sheets at opposite ends of said constriction ring, each one of said elastic sheets having a thickness of about 1 mm, a first one of said elastic sheets defining said peripheral openings, said central opening of said constriction ring having a diameter of about 10 mm.

98. The combination of claim 97, said constriction ring is attachable to said ring-shaped frame.

99. The combination of claim 98, wherein said first elastic sheet of said constriction ring has projections thereon extending outwardly.

100. The combination of claim 34, further comprising a massager, said massager including a motor, a battery for powering said motor, a switch for turning said motor on or off, one or more massaging flaps operatively connected to said motor for automatic massaging of a user during use.

101. The combination of claim 100, wherein each one of said massaging flaps has a width of about 1 inch, a length of about 0.75 inches.

102. The combination of claim 36, further comprising a lubricant delivery member attachable to said holder, said lubricant delivery member having a generally tubular and resilient wall extending between opposite first and second ends and defining a channel therebetween for reception of said sheath over said shaft, said wall further defining a chamber for storing a lubricant and a fluid conduit for releasing said lubricant onto said sheath received in said channel, said conduit is sized such that said lubricant is only released when a sufficient force is applied to said wall.

103. The combination of claim 34, wherein said prosthesis and said loose-fitting condom are attachable to each other.

104. An external penile prosthesis, comprising:
a generally tubular body portion extending about a central axis and having opposite first and second open ends for receiving a penis therein; and
a head portion attached to said first end of said body portion for covering the glans of said penis, said head portion extending along said central axis and comprising a plurality of flaps, each one of said flaps having a proximal end swingably attached to said body portion and a distal free end, said flaps swingable about an edge of said first end of said body portion between a closed position and an open position, wherein in said open position said free ends of said flaps define an opening and in said closed position said opening is at least partially closed.

* * * * *